United States Patent
Ostanin et al.

(10) Patent No.: US 7,223,533 B2
(45) Date of Patent: May 29, 2007

(54) CELL SURFACE PROTEINS AND USE THEREOF AS INDICATORS OF ACTIVATION OF CELLULAR SIGNAL TRANSDUCTION PATHWAYS

(75) Inventors: Kirill Ostanin, Salt Lake City, UT (US); Mary Cismowski, San Diego, CA (US); Lauren Silverman, Ossining, NY (US)

(73) Assignee: Cadus Technologies, Inc., New York, NY (US)

( * ) Notice: Subject to any disclaimer, the term of this patent is extended or adjusted under 35 U.S.C. 154(b) by 287 days.

(21) Appl. No.: 10/729,576

(22) Filed: Dec. 1, 2003

(65) Prior Publication Data

US 2005/0196743 A1 Sep. 8, 2005

Related U.S. Application Data

(63) Continuation of application No. 09/658,765, filed on Sep. 8, 2000, now abandoned.

(60) Provisional application No. 60/153,300, filed on Sep. 10, 1999.

(51) Int. Cl.
C12Q 1/00 (2006.01)
C12Q 1/68 (2006.01)
G01N 33/53 (2006.01)

(52) U.S. Cl. .............................. 435/4; 435/6; 435/7.1; 435/7.2; 435/7.31

(58) Field of Classification Search ...................... None
See application file for complete search history.

(56) References Cited

U.S. PATENT DOCUMENTS

| | | | | |
|---|---|---|---|---|
| 4,948,874 A | 8/1990 | Kronvall et al. | ............ | 350/350 |
| 5,096,815 A | 3/1992 | Ladner et al. | ............. | 435/69.1 |
| 5,283,173 A | 2/1994 | Fields et al. | .................. | 435/6 |
| 5,401,629 A | 3/1995 | Harpold et al. | ................ | 435/6 |
| 5,436,128 A | 7/1995 | Harpold et al. | ................ | 435/6 |
| 5,468,614 A | 11/1995 | Fields et al. | ................... | 435/6 |
| 5,482,835 A | 1/1996 | King et al. | ..................... | 435/6 |
| 5,576,210 A * | 11/1996 | Sledziewski et al. | .. | 435/254.21 |
| 5,580,736 A | 12/1996 | Brent et al. | ..................... | 435/6 |
| 5,691,188 A | 11/1997 | Pausch et al. | ........... | 435/225.1 |
| 5,739,029 A | 4/1998 | King et al. | ............ | 435/254.21 |
| 5,789,184 A | 8/1998 | Fowlkes et al. | ........... | 435/7.31 |
| 6,037,131 A * | 3/2000 | Reppert | ......................... | 435/6 |
| 6,100,042 A | 8/2000 | Fowlkes et al. | ............. | 435/7.1 |
| 6,159,705 A * | 12/2000 | Trueheart et al. | ............. | 435/29 |
| 6,251,605 B1 * | 6/2001 | Ostanin et al. | ................ | 435/6 |

FOREIGN PATENT DOCUMENTS

| | | |
|---|---|---|
| EP | 568925 | 11/1993 |
| WO | WO 88/10308 | 12/1988 |
| WO | WO 91/12273 | 8/1991 |
| WO | WO 92/05244 | 4/1992 |
| WO | WO 92/08740 | 5/1992 |
| WO | WO 93/10230 | 5/1993 |
| WO | WO 94/23025 | 10/1994 |
| WO | WO 95/30012 | 11/1995 |
| WO | WO 97/11159 | 3/1997 |
| WO | WO 98/13513 | 4/1998 |
| WO | WO 99/18211 | 4/1999 |

OTHER PUBLICATIONS

Alberts et al., Molecular Biology of the Cell, 2nd Edition, Chapter 4, pp. 177-178, Garland Publishing, Inc, 1989.*
Wojciechowicz et al., Cell surface anchorage and ligand-binding domains of the *saccharomyces cerevisiae* cell adhesion protein alpha-agglutinin, a member of the immunoglobulin superfamily. Mol. Cell. Biol. 13:2554-2563, 1993.*
Cappellaro et al., *Saccharomyces cerevisiae* a- and alpha-agglutinin: characterization of their molecular interaction. EMBO J. 10:4081-4088, 1991.*
Wu et al., A high-throughput STAT binding assay using fluorescence polarization. Analytical Biochemistry, 249;29-36, 1997.*
Akada, R. et al. "Genetic Relationships Between the G Protein βγ Complex, Ste5p, Ste20p and Cdc42p: Investigation of Effector Roles in the Yeast Pheromone Response Pathway," *Genetics* 143:103-117 (1996).
Alison, Malcolm R. et al. "Growth factors and growth factor receptors," *Brit. J. of Hosp. Med.* 49(11):774-88 (1993).
Altieri, Dario C. "Proteases and protease receptors in modulation of leukocyte effector functions," *J. of Leukocyte Biol.* 58:120-27 (1995).
Artemyev, Nikolai O. et al. "Sites of Interaction between Rod G-Protein α-Subunit and cGMP-phosphodiesterase γ-Subunit," *J. Biol. Chem.* 267(35):25067-72 (1992).
Awramik, S. M. "New fossil finds in old rocks," *Nature* 319:446-47 (1986).
Belka, C. et al. "The role of tyrosine kinases and their substrates in signal transmission of hematopoietic growth factors: a short review," *Leukemia* 9:754-61 (1995).
Bender, Alan and Sprague, George F. Jr. "Pheromones and Pheromone Receptors Are the Primary Determinants of Mating Specificity in the Yeast *Saccharomyces cerevisiae*," *Genetics* 121:463-76 (1989).

(Continued)

*Primary Examiner*—Ruixiang Li
(74) *Attorney, Agent, or Firm*—Edwards Angell Palmer & Dodge LLP; Peter C. Lauro, Esq.

(57) ABSTRACT

The present invention makes available a rapid, reproducible, robust assay system for screening and identifying pharmaceutically effective compounds that specifically interact with and modulate the activity of a cellular protein, e.g., a receptor or ion channel. The subject assay enables rapid screening of large numbers of compounds to identify those which act as an agonist or antagonist to the bioactivity of the cellular protein. In this system, the cell is treated with a compound, and functional interaction of this compound with a cellular receptor yields a detectable signal, which can be specifically measured. The subject assays include methods of identifying compounds which specifically modulate, for example, heterologous receptors coupled to the pheromone response pathway in yeast. The subject assays are particularly amenable to the identification of specific agonists and antagonists of G protein-coupled receptors.

15 Claims, No Drawings

OTHER PUBLICATIONS

Bimbaumer, Lutz "Transduction of receptor signal into modulation of effector activity by G protein: the first 20 years or so . . ." *FASEB Journal* 4:3178-88 (1990).

Blinder, Dmitry et al. "Constitutive Mutants in the Yeast Pheromone Response: Ordered function of the Gene Products," *Cell* 56:479-486 (1989).

Brill, Julie A. et al. "A Role for Autophosphorylation Revealed by Activated Alleles of *FUS3*, the Yeast MAP Kinase Homolog," *Molecular Biology of the Cell* 5:297-312 (1994).

Brugarolas, James et al. "Radiation-induced cell cycle arrest compromised by p21 deficiency," *Nature* 377:522-57 (1995).

Burack, W. Richard et al. "The Activating Dual Phosphorylation of MAPK by MEK Is Nonprocessive," *Biochemistry* 36(20):5929-5933 (1997).

Cavallini, Bruno et al. "A yeast activity can substitute for the HeLa Cell TATA box factor," *Nature* 334:77-80 (1988).

Chambers, D. A. et al. "Neuroimmuno Modulation: Signal Tranduction and Catecholamines," *Neurochem. Int.* 22(2):95-110 (1993).

Chan, Russell K. and Otte, Carol A. "Isolation and Genetic Analysis of *Saccharomyces cerevisiae* Mutants Supersensitive to G1 Arrest by a Factor a α Factor," *Molecular and Cellular Biol.* 2(1):11-20 (1982).

Chang, Fred and Herskowitz, Ira "Identification of a Gene Necessary for Cell Cycle Arrest by a Negative Growth Factor of Yeast: FAR1 is an Inhibitor of a G1 Cyclin, CLN2," *Cell* 63:999-1011 (1990).

Chien, Cheng-Ting, et al. "The two-hybrid system: A method to identify and clone genes for proteins that interact with a protein of interest," *Proc. Natl. Acad. Sci. USA* 88:9578-82 (1991).

Clark, Karen L. et al. "Interactions among the Subunits of the G-protein Involved in *Saccharomyces cerevisiae* Mating," *Molecular and Cellular Biol.* 13(1):1-8 (1993).

Cole, Gary M. et al. "Stoichiometry of G Protein Subunits Affects the *Saccharomyces cerevisiae* Mating Pheromone Signal Transduction Pathway," *Molecular and Cellular Biology* 10(2):510-517 (1990).

Coleman, David E. et al. "Structures of Active Conformation of $G_{i\alpha1}$ and the Mechanism of GTP Hydrolysis," *Science* 265:1405-12 (1994).

Conklin, Bruce R. et al. "Substitution of three amino acids switches receptor specificity of $G_{q\alpha}$ to that of $G_{i\alpha}$," *Nature* 363:274-76 (1993).

Cwirla, Steven E. et al. "Peptides of phage: A vast library of peptides for identifying ligands," *Proc. Natl. Acad. Sci. USA* 87:6378-82 (1990).

Devlin, James J. et al. "Random Peptide Libraries: A Source of Specific Protein Binding Molecules," *Science* 249:404-6 (1990).

Dietzel, Christine and Kurjan, Janet "The Yeast SCG1 Gene: A Gα-like Protein Implicated in the a- and α-factor Response Pathway," *Cell* 50:1001-10 (1987).

Dmochowska, Aleksandra et al. "Yeast *KEX1* Gene Encodes a Putative Protease with a Carboxypeptidase B-like Function Involed in Killer Toxin and α-Factor Precursor Processing," *Cell* 50:573-84 (1987).

Dolan, J. W. et al. "Overproduction of the yeast STE12 protein leads to constitutive transcriptional induction," *Genes & Development* 4(4):492-502 (1990).

Dubois, Patrice M. et al. "Role of the transmembrane and cytoplasmic domains of surface IgM in endocytosis and signal transduction," *Eur. J. Immunol.* 22:851-57 (1992).

Erickson, Deborah "Intercepted Messages: New biotechnology drugs target intracellular communication," *Scientific American* 267(5):122-23 (1992).

Etienne, Gilles et al. "A Screening Method for Antifungal Substances Using *Saccharomyces cerevisiae* Strains Resistant to Polyene Macrolides," *J. of Antibiotics* 43(2):199-206 (1990).

Fasullo, Michael T. and Davis, Ronald W. "Direction of Chromosome Rearrangements in *Saccharomyces cerevisiae* by Use of *his3* Recombination Substrates," *Molecular and Cellular Biol.* 8(10):4370-80 (1988).

Ferrell, James E. Jr. et al. "The Biochemical Basis of an All-or-None Cell Fate Switch in *Xenopus* Oocytes," *Science* 280:895-898 (1998).

Ferrell, James E. Jr. "Tripping the switch fantastic: how a protein kinase cascade can convert graded inputs into switch-like outputs," *Trends in Biochem. Sci.* 21(12):460-6 (1996).

Fields, Stanley and Song Ok-kyu "A novel genetic system to detect protein-protein interactions," *Nature* 340:245-46 (1989).

Franke, Arthur E. et al. "Human C5a Anaphylatoxin: Gene Synthesis, Expression, and Recovery of Biologically Active Material from *Escherichia coli,*" *Methods in Enzymology* 162:653-68 (1988).

Funaro, Ana et al. "Human CD38 is associated to distinct molecules which mediate transmembrane signaling in different lineages," *Eur. J. Immunol.* 23:2407-11 (1993).

Gallego, Carme et al. "Myristoylation of the $G_{\alpha i2}$ polypeptide, a G protein α subunit, is required for its signaling and transformation functions," *Proc. Natl. Acad. Sci. USA* 89:9695-99 (1992).

Garritsen, Anja et al. "The N-Terminal coiled-coil domain of β is essential for γ association: A Model for G-Protein βγ subunit interaction," *Proc. Natl. Acad. Sci. USA* 90:7706-10 (1993).

Gerard, Norma P. and Gerard, Craig "Construction and Expression of a Novel Recombinant Anaphylatoxin, C5a-N19, a Probe for the Human C5a Receptor," *Biochemistry* 29(39):9274-81 (1990).

Gordon, J. "B-cell signaling via the C-type lectins CD23 and CD72," *Immunology Today* 15(9):411-17 (1994).

Graf, Rolf et al. "A Truncated Recombinant α Subunit of $G_{i3}$ with a Reduced Affinity for βγ Dimers and Altered Guanosine 5'-O-(Thio)triphosphate Binding," *J. of Biol. Chem.* 267(34):24307-14 (1992).

Gros, Philippe et al. "Mammalian Multidrug Resistence Gene: Complete cDNA Sequence Indicates Strong Homology to Bacterial Transport Proteins," *Cell* 47:371-80 (1986).

Gyuris, Jenö et al. "Cdi1, A Human G1 and S Phase Protein Phosphatase That Associates with Cdk2," *Cell* 75:791-803 (1993).

Hagen, David C. et al. "Evidence the yeast *STE3* gene encodes a receptor for the peptide pheromone a factor: Gene sequence and implications for the structure of the presumed receptor," *Proc. Natl. Acad. Sci. USA* 83:1418-22 (1986).

Hall, Marcia et al. "Evidence for different modes of action of cyclin-dependent kinase inhibitors: p15 and p16 bind to kinases, p21 and p27 bind to cyclins," *Oncogene* 11:1581-88 (1995).

Harbury, Pehr B. et al. "A Switch Between Two-, Three- and Four-Stranded Coiled Coils in GCN4 Leucine Zipper Mutants," *Science* 262:1401-07 (1993).

Hartwell, Leland H. "Mutants of *Saccharomyces cerevisiae* Unresponsive to Cell Division Control by Polypeptide Mating Hormone," *J. Cell Biol.* 85:811-22 (1980).

Hasson, M.S. et al. "Mutational Activation of the *STE5* Gene Product Bypasses the Requirement for G Protein β and γ Subunits in the Yeast Pheromone Response Pathway," *Molecular and Cellular Biology* 14(2):1054-1065 (1994).

He, Bin et al. "*RAM2*, an essential gene of yeast, and *RAM1* encode the two polyeptide components of the farnesyltransferase that prenylates a-actor and Ras proteins," *Proc. Natl. Acad. Sci. USA* 88:11373-77 (1991).

Hiltunen, J. Kalervo et al. "Peroxisomal Multifunctional β-Oxidation Protein of *Saccharomyces cerevisiae,*" *J. of Biol. Chem.* 267(10):6646-6653 (1992).

Hrycyna, Christine A. et al. "The *Saccharomyces cerevisiae STE14* gene encodes a methyltransferase that mediates C-terminal methylation of a-factor and RAS Proteins," *The EMBO J.* 10(1):1699-1709 (1991).

Huang, Chi-Ying F. et al. "Ultrasensitivity in the mitogen-activated protein kinase cascade," *Proc. Natl. Acad. Sci. USA* 93:10078-10083 (1996).

Hughes, David A. et al. "Complementation of *byr1* in fission yeast by mammalian MAP kinase kinase requires coexpression of Raf kinase," *Nature* 364:349-52 (1993).

Imamoto, Akira et al. "Genetics of signal transduction: tales from the mouse," *Curr. Opin. Gen. & Dev.* 4:40-46 (1994).

Inouye, Carla et al. "Ste5 RING-H2 Domain: Role in Ste4-Promoted Oligomerization for Yeast Pheromone Signaling," *Science* 278:103-106 (1997).

Jabbar, M. Abdul et al. "Influenza Viral (A/WSN/33) hemagglutinin is expressed and glycosylated in the yeast *Saccharomyces cerevisiae*," *Proc. Natl. Acad. Sci. USA* 82:2019-23 (1985).

Jakobs, K. H. et al. "Dual regulation of adenylate cyclase. A signal transduction mechanism of membrane receptors," *Basic Res. Cardiol.* 81:1-9 (1986).

Journot, Laurent et al. "Amino Acids 367-376 of the $G_s$ α subunit induce membrane association when fused to soluble amino-terminal deleted $G_{i1}$ a subunit," *Proc. Natl. Acad. Sci. USA* 88:10054-58 (1991).

Julius, David et al. "Glycosylation and Processing of Prepro-α-Factor through the Yeast Secretory Pathway," *Cell* 36:309-18 (1984).

Julius, David et al. "Isolation of the Putative Structural Gene for the Lysine-Arginine-Cleaving Endopeptidase Required for Processing of Yeast Prepro-α-factor," *Cell* 37:1075-89 (1984).

Julius, David et al. "Yeast α Factor is Processed from a Larger Precursor Polypeptide: The Essential Role of a Membrane-Bound Dipeptidyl Aminopeptidase," *Cell* 32:839-52 (1983).

Kaiser, Chris A. et al. "Many Random Sequences Functionally Replace the Secretion Signal Sequence of Yeast Invertase," *Science* 235:312-17 (1987).

Kang, Yoon-Se et al. "Effects of expression of mammalian Gα and hybrid mammalian-yeast Gα proteins on the yeast pheromone response signal transduction pathway," *Molecular and Cellular Biology* 10(6):2582-90 (1990).

King, Klim et al. "Control of Yeast Mating Signal Transduction by Mammalian $β_2$-Adrenergic Receptor and $G_S$ α Subunit," *Science* 250:121-23 (1990).

Kingsman, S.M. et al. "The production of mammalian protein in *Saccharomyces cerevisiae*," *Tibtech* 5:53-57 (1987).

Koff, Andrew et al. "Human Cyclin E, a New Cyclin That Interacts with Two Members of the *CDC2* Gene Family," *Cell* 66:1217-28 (1991).

Kosugi, Shinji et al. "Characterization of heterogeneous mutations causing constitutive activation of the luteinizing hormone receptor in familial male precocious puberty," *Human Molecular Genetics* 4(2):183-88 (1995).

Kramer, R. A. et al. "HTLV-III *gag* Protein Is Processed in Yeast Cells by the Virus *pol*-Protease," *Science* 231:1580-85 (1986).

Kuchler, Karl and Thorner, Jeremy "Functional expression of human *mdr1* in the yeast *Saccharomyces cerevisiae*," *Proc. Natl. Acad. Sci. USA* 89:2302-06 (1992).

Kuchler, Karl et al. "*Saccharomyces cerevisiae* STE6 gene product: a novel pathway for protein export in eukaryotic cells," *The EMBO J.* 8(13):3973-84 (1989).

Kurjan, Janet "α-Factor Structural Gene Mutations in *Saccharomyces cerevisiae*: Effects on α-Factor Production and Mating," *Molecular and Cellular Biol.* 5(4):787-96 (1985).

Kurjan, Janet and Herskowitz "Structure of a Yeast Pheromone Gene (*MFα*): A Putative α-Factor Precursor Contains Four Random Copies of Mature α-Factor," *Cell* 30:933-43 (1982).

Lambright, David G. et al. "Structural determinants for activation of the α-subunit of a heterotrimeric G protein," *Nature* 369:621-28 (1994).

Leberer, Ekkehard et al. "Dominant-negative mutants of a yeast G-protein β subunit identify two functional regions involved in pheromone signaling," *The EMBO J.* 11(13):4805-13 (1992).

Lee, Ethan et al. The G22A Mutant of $G_{Sα}$ Highlights the Requirement for Dissociation of G Protein Subunits, *J. Biol. Chem.* 267(2):1212-18 (1992).

Lemire, Bernard D. et al. "The Mitochondrial Targeting Function of Randomly Generated Peptide Sequences Correlates with Predicted Helical Amphiphilicity," *J. Biol. Chem.* 264(34):20206-12 (1989).

Lew, Daniel J. et al. "Isolation of Three Novel Human Cyclins by Rescue of G1 Cyclin (Cln) Function in Yeast," *Cell* 66:1197-1206 (1991).

Linder, Maurine E. and Gilman, Alfred G. "G Proteins," *Scientific American* 267(1):56-65 (1992).

Linder, Maurine E. et al. "Lipid Modifications of G Protein Subunits: Myristoylation of $G_{Oα}$ Increased its Affinity for βγ," *J. Biol. Chem.* 266(7):4654-59 (1991).

Lupas, Andrei N. et al. "Do G protein subunits associate via a three-stranded coiled coil?" *FEBS* 314(2):105-08 (1992).

Mackay, Vivian and Manney, Thomas R. "Mutations Affecting Sexual Conjugation and Related Processes in *Saccharomyces cerevisiae*. II Genetic Analysis of Nonmating Mutants," *Genetics* 76:273-88 (1974).

Marengere, Luc E.M. and Pawson, Tony "Structure and function of SH2 domains," *J. Cell Science Suppl.* 18:97-104 (1994).

Markby, David W. et al. "Separate GTP Binding and GTPase Activating Domains of a Gα Subunit," *Science* 262:1895-1901 (1993).

Michaelis, Susan and Herskowitz, Ira "The a-Factor Pheromone of *Saccharomyces cerevisiae* is Essential for Mating," *Molecular and Cellular Biol.* 8(3):1309-18 (1988).

Milano, C.A. et al. "Enhanced Mycardial Function in Transgenic Mice Overexpressing the $β_2$-Adrenergic Receptor," *Science* 264:582-86 (1994).

Milburn, Michael V. et al. "Molecular Switch for Signal Transduction: Structural Differences Between Active and Inactive Forms of Protooncogenic *ras* Proteins," *Science* 247:939-45 (1990).

Mumby, Susanne M. et al. "G-Protein α-subunit expression, myristoylation, and membrane association in COC cells," *Proc. Natl. Acad. Sci. USA* 87:728-32 (1990).

Murphy, A.J.M. et al. "Autocrine Stimulation of Yeast through Human G-Coupled Receptors," *J. Cell Biochem.* 18B:224 (1994).

Nakafuku, Masato et al. "Occurrence in *Saccharomyces cerevisiae* of a gene homologous to the cDNA coding for the α-subunit of mammalian G proteins," *Proc. Natl. Acad. Sci. USA* 84:2140-44 (1987).

Nakayama, N. et al. "Common signal transduction system shared by STE2 and STE3 in haploid cells of *Saccharomyces cerevisiae*: autocrine cell-cycle arrest results from forced expression of *STE2*," *The EMBO J.* 6(1):249-54 (1987).

Neer, Eva J. et al. "The Amino Terminus of a G Protein α Subunits Is Required for Interaction with βγ," *J. Biol. Chem.* 263(18):8996-9000 (1988).

Noel, Joseph P. et al. "The 2.2 Å crystal structure of transducin-α complexed with GTP-γ-S," *Nature* 366:654-63 (1993).

Noelle, Randolph J. et al. "CD40 and its ligand, an essential ligand-receptor pair for thymus-dependent B-cell activation," *Immuno. Today* 13(11):431-33 (1992).

Nomoto, Satoshi et al. "Regulation of the yeast pheromone response pathway by G protein subunits," *The EMBO J.* 9(3):691-696 (1990).

Nye, Jeffrey S. and Kopan, Raphael "Vertebrate ligands for Notch," *Current Biology* 5(9):966-69 (1995).

Oeda, Kenji et al. "Expression of Rat Liver Cytochrome P-450MC cDNA in *Saccharomyces cerevisiae*," *DNA* 4(3):203-10 (1985).

Ogden, Jill E. et al. "Efficient Expression of the *Saccharomyces cerevisiae* PGK Gene Depends on an Upstream Activation Sequence by Does Not Require TATA Sequences," *Molecular and Cellular Biol.* 6(12):4335-43 (1986).

Pronin, Alexey N. and Gautam, Narasimhan "Interaction between G-Protein β and γ subunit types is selective," *Proc. Natl. Acad. Sci. USA* 89:6220-24 (1992).

Ramer, Sandra W. and Davis, Ronald W. "A dominant truncation allele identifies a gene, *STE20*, that encodes a putative protein kinase necessary for mating in *Saccharomyces cerevisiae*," *Proc. Natl. Acad. Sci. USA* 90:452-456 (1993).

Ranade, Koustubh et al. "Mutations associated with familial melanome impair $p16^{INK4}$ function," *Nature Genetics* 10:114-16 (1995).

Rarick, Helen M. et al. "A Site of Rod G Protein α Subunit That Mediates Effector Activation," *Science* 256:1031-33 (1992).

Raymond, Martine et al. "Functional Complemetation of Yeast *ste6* by a Mammalian Multidrug Resistence *mdr* Gene," *Science* 256:232-34 (1992).

Reed, Randall R. "G Protein Diversity and the Regulation of Signaling Pathways," *The New Biologist* 2(11):957-60 (1990).

Schafer, William R. et al. "Enzymatic Coupling of Cholesterol Intermediates to a Mating Pheromone Precursor and to the Ras Protein," *Science* 249:1133-39 (1990).

Schafer, William R. et al. "Genetic and Pharmacological Suppression of Oncogenic Mutations in *RAS* Genes of Yeast and Humans," *Science* 245:379-85 (1989).

Schärer, E. and Iggo, R. "Mammalian p53 can function as a transcription factor in yeast," *Nucleic Acids Research* 20(7):1539-45 (1992).

Scott, Jamie K. and Smith, George P. "Searching for Peptide Ligands with an Epitope Library," *Science* 249:386-90 (1990).

Sikorski, Robert S. and Hieter, Philip "A System of Shutte Vectors and Yeast Host Strains Designed for Efficient Manipulation of DNA in *Saccharomyces cerevisiae*," *Genetics* 122:19-27 (1989).

Singh, Arjun et al. "*Saccharomyces cerevisiae* contains two discrete genes coding for the α-factor pheromone," *Nucleic Acids Research* 11(12):4049-63 (1983).

Slepak, Vladlen Z. et al. "Mutational Analysis of G Protein α Subunit $G_{O\alpha}$ Expressed in *Escherichia coli*," *J. Biol. Chem.* 268(2):1414-23 (1993).

Spiegel, Allen M. et al. "The G protein connection: molecular basis of membrane association," *TIBS* 16:338-41 (1991).

Steube, Klaus et al. "α-Factor-leader-directed secretion of recombinant human-insulin-like growth factor I from *Saccharomyces cerevisiae*," *Eur. J. Biochem.* 198:651-57 (1991).

Stevenson, Brian J. et al. "Constitutive mutants of the Protein Kinase STE11 Activate the Yeast Pheromone Response Pathway in the Absence of the G Protein," *Genes & Development* 6:1293-1304 (1992).

Strubin, Michel and Struhl, Kevin "Yeast and Human TFIID with Altered DNA-Binding Specificity of TATA Elements," *Cell* 68:721-30 (1992).

Struhl, Kevin "Constitutive and Inducible *Saccharomyces cerevisiae* Promoters: Evidence for Two Distinct Molecular Mechanisms," *Molecular and Cellular Biol.* 6(11):3847-53 (1986).

Struhl, Kevin et al. "High-frequency transformation of yeast: Autonomous replication of hybrid DNA molecules," *Proc. Natl. Acad. Sci. USA* 76(3):1035-39 (1979).

Struhl, Kevin and Hill, David E. "Two Related Regulatory Sequences are Required for Maximal Induction of *Saccharomyces cerevisiae his3* Transcription," *Molecular and Cellular Biol.* 7(1):104-10 (1987).

Sullivan, Kathleen A. et al., "Identification of receptor contact site involved in receptor-G protein coupling," *Nature* 330:758-60 (1987).

Suzuki, Takeshi et al. "HTLV-1 Tax protein interacts with cyclin-dependent kinase inhibitor $p16^{INK4A}$ and counteracts its inhibitory activity towards CDK4," *The EMBO J.* 15(7):1607-14 (1996).

Teem, John L. et al. "Indentification of Revertans for the Cystic Fibrosis ΔF508 Mutation Using STE6-CFTR Chimeras in Yeast," *Cell* 73:335-346 (1993).

Thomas, Thomas C. et al. "G-protein $α_0$ subunit: Mutation of conserved cysteines identifies a subunit contact surface and alters GDP affinity," *Proc. Natl. Acad. Sci. USA* 90:10295-99 (1993).

Tyson, John J. et al. "Chemical kinetic theory: understanding cell-cycle regulation," *Trends in Biochem. Sci.* 21:89-96 (1996).

Walker, John E. et al. "Distantly related requences in the α-and β-subunits of ATP synthase, myosin, kinases and other ATP-requiring enzymes and a common nucleotide binding fold," *The EMBO J.* 1(8):945-51 (1982).

Waters, M. Gerard et al. "Prepro-α-factor Has a Cleavable Signal Sequence," *J. Biol. Chem.* 263(13):6209-14 (1988).

Whiteway, Malcolm S. et al. "Association of the Yeast Pheromone Response G Protein βγ Subunits with the MAP Kinase Scaffold Ste5p," *Science* 269:1572-1575 (1995).

Whiteway, Malcolm et al. "Dominant negative selection of heterologous genes: Isolation of *Candida albicans* genes that interfere with *Saccharomyces cerevisiae* mating factor-induced cell cycle arrest," *Proc. Natl. Acad. Sci. USA* 89:9410-14 (1992).

Whiteway, Malcolm et al. "Genetic Identification of Residues Involved in Association of α and β G-Protein Subunits," *Molecular and Cellular Biol.* 14(5):3223-3229 (1994).

Whiteway, Malcolm et al. "The *STE4* and *STE18* Genes of Yeast Encode Potential β and γ Subunits of the Mating Factor Receptor-Coupled G Protein," *Cell* 56:467-477 (1989).

Wolowiec, D. et al. "Expression of cell cycle regulatory proteins in chronic lymphotic leukemias. Comparison with non-Hodgkin's lymphomas and non-neoplastic lymphoid tissue," *Leukemia* 9:1382-88 (1995).

Xiong, Yue et al. "Alteration of Cell Cycle Kinase Complexes in Human Papillomavirus E6- and E7- Expressing Fibroblasts Precedes Neoplastic Transformation," *J. Virology* 70(2):999-1008 (1996).

Xiong, Yue et al. "Human D-Type Cyclin," *Cell* 65:691-99 (1991).

Zervos, Antonis S. et al. "Mxi1, a Protein that Specifically Interacts with Max to Bind Myc-Max Recognition Sites," *Cell* 72:223-32 (1993).

Zhan, Xiao-Li et al. "Differential regulation of *FUS3* MAP kinase by tyrosine-specific phosphatases *PTP2/PTP3* and dual-specificity phosphatase *MSG5* in *Saccharomyces cerevisiae*," *Genes & Development* 11:1690-1702 (1997).

Lolait, Stephen J. et al., "Extrapituitary expression of the rat V1b vasopression receptor gene." *Proc. Natl. Acad. Sci.*, vol. 92, Jul. 1995; pp. 6783-6787.

* cited by examiner

CELL SURFACE PROTEINS AND USE THEREOF AS INDICATORS OF ACTIVATION OF CELLULAR SIGNAL TRANSDUCTION PATHWAYS

RELATED APPLICATIONS

This application is a continuation application of application Ser. No. 09/658,765, filed Sep. 8, 2000, now abandoned, which claims priority to provisional application No. 60/153,300, filed Sep. 10, 1999. The contents of the aforementioned applications are hereby incorporated by reference.

FIELD OF THE INVENTION

The invention is related to the detection of the transduction of an extracellular signal by an intracellular signal transduction pathway. In particular, the invention relates to methods and compositions useful for identifying a test compound as an agonist or antagonist of a cellular receptor.

BACKGROUND OF THE INVENTION

The identification of biological activity in new molecules has historically been accomplished through the use of in vitro assays or whole animals. Intact biological entities, either cells or whole organisms, have been used to screen for anti-bacterial, anti-fungal, anti-parasitic and anti-viral agents in vitro. Cultured mammalian cells have also been used in screens designed to detect potential therapeutic compounds. A variety of bioassay endpoints have been exploited in cell screens including the stimulation of growth or differentiation of cells, changes in cell motility, the production of particular metabolites, the expression of specific proteins within cells, altered protein function, and altered conductance properties. Cytotoxic compounds used in cancer chemotherapy have been identified through their ability to inhibit the growth of tumor cells in vitro and in vivo. In addition to cultures of dispersed cells, whole tissues have served in bioassays, as in those based on the contractility of muscle.

In vitro testing is a preferred methodology in that it permits the design of high-throughput screens: small quantities of large numbers of compounds can be tested in a short period of time and at low expense. Optimally, animals are reserved for the latter stages of compound evaluation and are not used in the discovery phase, inasmuch as the use of whole animals is labor-intensive and extremely expensive.

The search for agonists and antagonists of cellular receptors has been an intense area of research aimed at drug discovery because of the elegant specificity of these molecular targets. Drug screening has been carried out using whole cells expressing functional receptors and, recently, binding assays employing membrane fractions or purified receptors have been designed to screen compound libraries for competitive ligands.

G protein-coupled receptors (GPCRs) are a particularly important category of cell surface receptors. The medical importance of these receptors is evidenced by the fact that more than 60% of all commercially available prescription drugs work by interacting with known GPCRs. Hundreds, if not thousands, of receptors convey messages through heterotrimeric G proteins, of which at least 17 distinct forms have been isolated. Most G protein-coupled receptors are comprised of a single protein chain that is threaded through the plasma membrane seven times. Such receptors are often referred to as seven-transmembrane receptors (STRs). More than a hundred different GPCRs have been found, including many distinct receptors that bind the same ligand, and there are likely many more GPCRs awaiting discovery. The development of new drug discovery assays to identify novel modulators of GPCRs would be of tremendous benefit.

The heterologous expression of recombinant mammalian G protein-coupled receptors in mammalian cells which do not normally express those receptors has been described as a means of studying receptor function for the purpose of identifying agonists and antagonists of those receptors. For example, the human muscarinic receptor (HM1) has been functionally expressed in mouse cells (Harpold et al. U.S. Pat. No. 5,401,629). The rat V1b vasopressin receptor has been found to stimulate phosphotidylinositol hydrolysis and intracellular $Ca^{2+}$ mobilization in Chinese hamster ovary cells upon agonist stimulation (Lolait et al. (1995) *Proc. Natl. Acad. Sci. USA* 92:6783–6787). These types of ectopic expression studies have enabled researchers to study receptor signaling mechanisms and to perform mutagenesis studies which have been useful in identifying portions of receptors that are critical for ligand binding or signal transduction.

Experiments have also been undertaken to express functional G protein-coupled receptors in yeast cells. For example, U.S. Pat. No. 5,482,835 to King et al. describes a transformed yeast cell which is incapable of producing a yeast G protein α subunit, but which has been engineered to produce both a mammalian G protein α-subunit and a mammalian receptor which is "coupled to" (i.e., interacts with) the aforementioned mammalian G protein α-subunit. Specifically, U.S. Pat. No. 5,482,835 reports expression of the human beta-2 adrenergic receptor (β2AR), a seven transmembrane receptor (STR), in yeast, under control of the GAL1 promoter, with the β2AR gene modified by replacing the first 63 base pairs of coding sequence with 11 base pairs of noncoding and 42 base pairs of coding sequence from the STE2 gene. (STE2 encodes the yeast α-factor receptor.) It was found that the modified β2AR was functionally integrated into the membrane, as shown by studies of the ability of isolated membranes to interact properly with various known agonists and antagonists of β2AR. The ligand binding affinity for yeast-expressed β2AR was said to be nearly identical to that observed for naturally produced β2AR.

U.S. Pat. No. 5,482,835 also describes co-expression of a rat G protein α-subunit in yeast strain 8C, which lacks the cognate yeast protein. Ligand binding resulted in G protein-mediated signal transduction. U.S. Pat. No. 5,482,835 further teaches that these cells may be used in screening compounds for the ability to affect the rate of dissociation of Gα from Gβγ in a cell. For this purpose, the cell further contains a pheromone-responsive promoter (e.g., BAR1 or FUS1), linked to an indicator gene (e.g. HIS3 or lacZ). The cells are placed in multi-titer plates, and different compounds are placed in each well. The colonies are then scored for expression of the indicator gene.

U.S. Pat. No. 5,789,184 describes yeast cells engineered to express a heterologous kinase as a yeast pheromone system protein surrogate, and a heterologous polypeptide. The yeast cells are used in assays to screen for peptides that modulate the activity of non-yeast surrogates.

U.S. Pat. No. 5,879,591 describes yeast cells engineered to express a heterologous protein (e.g., a farnesyl transferase) which functions as a surrogate for, and performs the function of, a yeast pheromone system protein, as well as a heterologous polypeptide. The yeast cells are useful in screening assays to identify polypeptides which modulate the interaction of the surrogate with the yeast pheromone system.

U.S. Ser. No. 08/322,137 describes yeast cells engineered to express both a surrogate, e.g., a G protein-coupled receptor, of a pheromone pathway component and a potential peptide modulator of the surrogate. This is performed in such a manner that inhibition or antagonism of the surrogate by the peptide modulator affects a screenable or selectable trait of the yeast cell. Also included are mechanisms by which the signal-to-noise ratio of the system may be improved. The yeast cells are useful in assays to screen for peptides that modulate the activity of endogenous and heterologous yeast pheromone system surrogates.

Published PCT international application WO 98/13513 describes methods for identifying modulators of heterologous receptors expressed in yeast. Modulators are identified by detecting an alteration in a signal produced by an endogenous yeast signaling pathway.

Published PCT international application WO 99/18211 describes novel yeast cells which express a heterologous G protein coupled receptor and mutant and/or chimeric G protein subunit molecules which serve to functionally integrate the heterologous receptor into the pheromone signaling pathway of the yeast cell.

SUMMARY OF THE INVENTION

It is an object of the present invention to provide a novel, reproducible, robust assay system for screening and identifying pharmaceutically effective compounds that specifically interact with and modulate the activity of a cellular receptor or ion channel of a cell. More particularly, the invention provides a highly sensitive assay system for the identification of agonist or antagonist activity of a test compound for a specific receptor.

In one embodiment, the invention provides a method for identifying a test compound that modulates a heterologous receptor in a cells, in which is provided a cell containing a heterologous receptor that is functionally integrated into a cellular signal transduction pathway, such that upon activation of the signal transduction pathway, a detectable signal is presented at the cell surface. By contacting the cell with a test compound and detecting the level of expression of the detectable signal, the ability of the compound to modulate signaling via the heterologous receptor can be measured. In a preferred embodiment, the cell is a yeast cell. In a particularly preferred embodiment, the cell is a MATa *Saccharomyces cerevisiae* cell. In another preferred embodiment, the signal transduction pathway is a yeast pheromone response pathway. In another particularly preferred embodiment, the detectable signal is the protein product of the AGA2 gene.

In another embodiment, the invention provides a method for identifying a test compound that modulates a heterologous receptor in a cell, the method comprising: providing a cell which includes a heterologous receptor that is functionally integrated into a signal transduction pathway of the cell, in which cell surface presentation of a detectable signal is induced upon activation of the signal transduction pathway; contacting the cell with a test compound; and detecting the level of expression of the detectable signal as a measure of the ability of the compound to modulate signaling via the heterologous receptor. The detection step of the method includes incubating the cell with a detector molecule conjugated with a reporter moiety, where the detector molecule binds specifically to the detectable signal; washing the cell to remove unbound detector molecules; incubating the cell with a substrate appropriate for the reporter moiety; and measuring the readout from the reporter moiety. In a preferred embodiment, the detector molecule is the Sag1 protein, with a protein comprising amino acids 20–352 of the mature Sag1 protein being particularly preferred. In another preferred embodiment, the reporter moiety is a reporter gene. In another particularly preferred embodiment, the reporter gene is selected from the group consisting of beta-lactamase, peroxidase, luciferase, and alkaline phosphatase.

In another embodiment, the invention provides a method for identifying a test compound that modulates a heterologous receptor in a cell, the method comprising: providing a cell which includes a heterologous receptor that is functionally integrated into a signal transduction pathway of the cell, in which cell surface presentation of a detectable signal is induced upon activation of the signal transduction pathway; contacting the cell with a test compound; and detecting the level of expression of the detectable signal as a measure of the ability of the compound to modulate signaling via the heterologous receptor. The detection step of the method includes: incubating the cell with a detector molecule conjugated with a reporter moiety, where the detector molecule binds specifically to the detectable signal; washing the cell to remove unbound detector molecules; and measuring the readout from the reporter moiety. In a preferred embodiment, the detector molecule is the Sag1 protein, with a protein comprising amino acids 20–352 of the mature Sag1 protein being particularly preferred. In another preferred embodiment, the reporter moiety is a fluorophore, and the readout measuring step includes a fluorescence polarization technique.

In another embodiment, the invention provides a method for identifying a test compound that modulates a heterologous receptor in a cell, the method comprising: providing a cell which includes a heterologous receptor that is functionally integrated into a signal transduction pathway of the cell, in which cell surface presentation of a detectable signal is induced upon activation of the signal transduction pathway; contacting the cell with a test compound; extracting the cell-surface expressed detectable signal, and detecting the level of expression of the detectable signal as a measure of the ability of the compound to modulate signaling via the heterologous receptor. In a preferred embodiment, the extraction step involves the treatment of the cell with a reducing agent.

In another embodiment, the invention provides a method for identifying a test compound that modulates a heterologous receptor in a cell, the method comprising: providing a cell which includes a heterologous receptor that is functionally integrated into a signal transduction pathway of the cell, in which cell surface presentation of a detectable signal is induced upon activation of the signal transduction pathway; contacting the cell with a test compound; extracting the cell-surface expressed detectable signal with a reducing agent, and detecting the level of expression of the detectable signal as a measure of the ability of the compound to modulate signaling via the heterologous receptor. The detection step involves: binding of the extracted detectable signal to a support; incubating the support with a detection molecule conjugated with a reporter moiety; and measuring the readout from the reporter moiety. In a particularly preferred embodiment, the support includes streptavidin-coated SPA beads containing scintillant, and the binding of the extracted detectable signal to the support is mediated by a biotinylated antibody, where the antibody binds specifically to the extracted detectable signal and also to the streptavidin-coated bead. In yet another preferred embodiment, the detection molecule is the Sag1 protein, with a protein comprising amino acids 20–352 of the mature Sag1 protein being particularly preferred. In another preferred embodiment, the reporter moiety is a radiolabel, with $^{125}I$ or $^{3}H$ being particularly preferred. In another preferred embodiment, the readout measuring step includes detection of emitted light.

In another embodiment, the invention provides a method for identifying a test compound that modulates a heterologous receptor in a MATa *Saccharomyces cerevisiae* cell, the method comprising: providing a MATa *Saccharomyces cerevisiae* cell which includes a heterologous receptor that is functionally integrated into a signal transduction pathway of the cell, in which cell surface presentation of a detectable signal is induced upon activation of the signal transduction pathway; contacting the cell with a test compound; and detecting the level of expression of the detectable signal as a measure of the ability of the compound to modulate signaling via the heterologous receptor. The MATa *Saccharomyces cerevisiae* cell of this method further is deleted for the endogenous AGA1 gene, such that the AGA2 gene product is secreted.

In another embodiment, the invention provides a method for identifying a test compound that modulates a heterologous receptor in a MATa *Saccharomyces cerevisiae* cell, the method comprising: providing a MATa *Saccharomyces cerevisiae* cell which includes a heterologous receptor that is functionally integrated into a signal transduction pathway of the cell, in which cell surface presentation of a detectable signal is induced upon activation of the signal transduction pathway; contacting the cell with a test compound; and detecting the level of expression of the detectable signal as a measure of the ability of the compound to modulate signaling via the heterologous receptor. The MATa *Saccharomyces cerevisiae* cell of this method further is deleted for the endogenous AGA1 gene, such that the AGA2 gene product is secreted. The detection step includes: binding of the secreted AGA2 gene product to a support; incubating the support with a detection molecule conjugated with a reporter moiety; and measuring the readout from the reporter moiety. In a preferred embodiment, the support includes streptavidin-coated SPA beads containing scintillant, and binding of the secreted Aga2 protein to the support is mediated by a biotinylated antibody, where the antibody binds specifically to the secreted Aga2 protein and also to the streptavidin-coated bead. In another preferred embodiment, the detection molecule is the Sag1 protein, with a protein comprising amino acids 20–352 of the mature Sag1 protein being particularly preferred. In another preferred embodiment, the reporter moiety is a radiolabel, with $^{125}I$ or $^{3}H$ being particularly preferred. In yet another preferred embodiment, the readout detection step comprises detection of emitted light.

In another embodiment, the invention provides a method for identifying a test compound that modulates a heterologous G-protein coupled receptor in a yeast cell, the method comprising: providing a yeast cell which includes a heterologous G-protein coupled receptor that is functionally integrated into a signal transduction pathway of the yeast cell, in which cell surface presentation of a detectable signal is induced upon activation of the signal transduction pathway; contacting the yeast cell with a test compound; and detecting the level of expression of the detectable signal as a measure of the ability of the compound to modulate signaling via the heterologous G-protein coupled receptor.

In a preferred embodiment, the heterologous G-protein coupled receptor is selected from the group consisting of melatonin receptor 1a, galanin receptor 1, neurotensin receptor, adenosine receptor 2a, somatostatin receptor 2, and corticotropin releasing factor receptor 1. In a particularly preferred embodiment, the heterologous receptor is melatonin receptor 1a. In another particularly preferred embodiment, the heterologous G-protein coupled receptor functionally couples to the endogenous yeast GPA-1 protein subunit.

In another embodiment, the invention provides a kit for screening of test compounds that modulate a heterologous receptor in a cell, containing a cell having a heterologous receptor that is functionally integrated into a cellular signal transduction pathway, such that a signal molecule is expressed on the cell surface upon activation of the signal transduction pathway, and a means for detecting the signal molecule. In a preferred embodiment, the kit further contains appropriate buffers and instructional materials for quantitating the detectable signal.

In another embodiment, the invention provides a kit for screening of test compounds that modulate a heterologous receptor in a cell, containing a cell having a heterologous receptor that is functionally integrated into a signal transduction pathway of the cell, such that a signal molecule is secreted from the cell upon activation of the signal transduction pathway, and a means for detecting the secreted signal molecule. In a preferred embodiment, the kit further contains appropriate buffers and instructional materials for quantitating the secreted signal molecule.

DETAILED DESCRIPTION OF THE INVENTION

Proliferation, differentiation and death of eukaryotic cells are controlled by a variety of extracellular signals, such as hormones, neurotransmitters, and polypeptide factors. These diffusible ligands allow cells to influence and be influenced by environmental cues. The study of receptor-ligand interaction has revealed a great deal of information about how cells respond to external stimuli, and this knowledge has led to the development of therapeutically important compounds.

The present invention makes available a rapid, effective assay for screening and identifying pharmaceutically effective compounds that specifically interact with and modulate the activity of a cellular receptor, ion channel, or a surrogate screening of large numbers of compounds including, for example, small organic molecules, or polypeptides in an expression library to identify compounds which induce or antagonize receptor bioactivity.

The assay of the present invention provides a convenient format for the discovery of drugs that can be useful to modulate cellular function, as well as to understand the pharmacology of compounds that specifically interact with cellular receptors, ion channels, and components that modulate a surrogate of the pheromone response pathway, e.g., kinases, farnesyl transferases, and ABC transporters. Moreover, the subject assay is particularly amenable to the identification of ligands, natural or artificial, for receptors and ion channels.

I. Definitions

Before further description of the invention, certain terms employed in the specification, examples and appended claims are, for convenience, collected here.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express a reporter gene construct, heterologous receptor or test polypeptide.

The terms "operatively linked", "operably linked" and "associated with" are used herein interchangeably and are intended to mean that molecules are functionally coupled to each other in that the change of activity or state of one molecule is affected by the activity or state of the other molecule. Typically, two polypeptides are covalently attached through peptide bonds.

The terms "protein" and "polypeptide" are used interchangeably herein. The term "peptide" is used herein to refer to a chain of two or more amino acids or amino acid analogs (including non-naturally occurring amino acids), with adjacent amino acids joined by peptide (—NHCO—) bonds. Thus, the peptides of the invention include oligopeptides, polypeptides, proteins, and peptidomimetics. Methods for preparing peptidomimetics are known in the art. In particular, a peptidomimetic can be derived as a retro-inverso analog of the peptide. Such retro-inverso analogs can be prepared according to methods known in the art (see, e.g., U.S. Pat. No. 4,522,752).

The term "conjugated with" as used herein refers to a linkage between two molecules, such that both remain associated. A polypeptide molecule conjugated with a reporter moiety maintains that association with the reporter even when the protein, e.g., binds to a receptor or a solid support. Examples of conjugated molecules include, but are not limited to, a polypeptide fused to another polypeptide, and a polypeptide tagged with a fluorophore or a radiolabel.

The term "reporter moiety" as used herein refers to a molecule which provides a detectable signal. Such molecules include, but are not limited to, polypeptides such as enzymes, which provide, e.g., a detectable colorimetric or luminescent signal upon incubation with an appropriate substrate. Other such molecules are radiolabels or fluorescent tags, the readout from which can be directly measured without a requirement for an additional substrate. Such molecules are well known in the prior art.

The term "activation" (as in "activation" of a pheromone response/signal transduction pathway of a yeast cell") is intended to refer to "switching on" the signal transduction cascade. The signal transduction cascade can be switched on by external signals that interact with cell receptors, e.g., ligand binding to a G protein-coupled receptor. The term "stimulation" is also intended to encompass switching on the signal transduction cascade by any other process including, for example, a process similar to the process by which phorbol esters activate the calcium dependent signal transduction pathway of T cell receptors.

The term "functionally integrated" (as in a receptor that is "functionally integrated into a signal transduction pathway in a cell" or "functionally integrated into a yeast pheromone response pathway") is intended to refer to the ability of the receptor to be expressed at the surface of the cell and the ability of the expressed receptor to bind to modulators (e.g., a ligand of the receptor) and transduce signals into the cell via components of a signal transduction pathway of the cell. For example, a G protein-coupled receptor (GPCR) which is functionally integrated into an endogenous pheromone response pathway of a yeast cell is expressed on the surface of the yeast cell, couples to a G protein of the pheromone response pathway within the yeast cell, and transduces a signal in that yeast cell upon binding of a modulator to the receptor.

The term "modulation" is intended to encompass, in its various grammatical forms (e.g., "modulated", "modulation", "modulating", etc.), up-regulation, induction, stimulation, potentiation, localization changes (e.g., movement of a protein from one cellular compartment to another) and/or relief of inhibition, as well as inhibition and/or down-regulation.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation. A "signal transduction pathway" refers to the components involved in "signal transduction" of a particular signal into a cell. The term "endogenous signal transduction pathway" indicates that some or all of the components of the signal transduction pathway are naturally-occurring components of the cell. An example of such a pathway is the endogenous pheromone response pathway of yeast.

The term "detectable signal", "secreted signal molecule", or "signal molecule" as used herein refers to a molecule or other element produced as a result of transduction of a signal through a signal transduction pathway. Such production may be direct or indirect, but in either case, the production of the detectable signal is an indicator that signaling through said signal transduction pathway has taken place. Such detectable signals may be, but are not limited to, polypeptides expressed upon signaling through the pathway, or they may take the form of small organic or inorganic molecules, such as oxygen radicals or ions. Emission of light or heat in response to signaling through a cellular pathway is also encompassed by this term.

The term "detecting an alteration in a signal produced by a signal transduction pathway" (e.g., a yeast pheromone response pathway) is intended to encompass the detection of alterations in second messengers produced upon activation of components of the signal transduction pathway, alterations in gene transcription induced upon activation of components of the signal transduction pathway, and/or alterations in the activity of a protein(s) upon activation of components of the signal transduction pathway. In some embodiments, the term "detecting an alteration in a signal produced by an endogenous signal pathway" is not, however, intended to encompass detecting alterations in the level of expression of an exogenous reporter gene that has been introduced into the cell or the activity of the reporter gene product. Moreover, the term "detecting an alteration in a signal produced by a signal transduction pathway" is not intended to encompass assaying general, global changes to the cell. Rather, this term indicates that a specific signal associated with the signal transduction pathway is assayed.

As used herein, the term "cell surface presentation" is intended to encompass both detectable signals which are secreted by and tethered to the surface of the cell, either through anchoring in the cellular membrane or by binding to a cell-surface protein, and also detectable signals which are secreted by and not tethered to the surface of the cell.

As used herein, the term "extracellular signal" is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

The term "detection molecule" as used herein refers to a compound which specifically interacts with the detectable signal. This compound can be, e.g., an antibody, or a natural ligand for the detectable signal. It is optionally conjugated with a reporter moiety.

The term "wild type protein" as used herein refers to unmodified, naturally occurring cellular proteins (e.g., a yeast protein) or fragments thereof.

The term "mutated protein" or "mutant protein" as used herein refers to a cellular proteins (e.g., a yeast protein), or fragment thereof, that has been modified by addition, deletion or substitution of amino acid residues in the protein. Preferably, the mutated protein is derived from the wild type protein.

The term "compound" as used herein (e.g., as in "test compound") is meant to include both exogenously added test compounds and peptides endogenously expressed from a peptide library. For example, in certain embodiments, the reagent cell also produces the test compound which is being screened. The reagent cell can produce, e.g., a test polypeptide, a test nucleic acid and/or a test carbohydrate which is screened for its ability to modulate the receptor/channel activity. In such embodiments, a culture of such reagent cells will collectively provide a library of potential effector molecules and those members of the library which either agonize or antagonize the receptor or ion channel function can be selected and identified. Moreover, it will be apparent that the reagent cell can be used to detect agents which transduce a signal via the receptor or channel of interest.

In other embodiments, the test compound is exogenously added. In such embodiments the test compound is contacted with the reagent cell. Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds, for example small organic molecules. "Non-peptidic compounds" also are intended to include natural products.

The term "receptor effector" is intended to include agonists and antagonists that modulate signal transduction via a receptor. Receptor effector molecules are capable of binding to the receptor, though not necessarily at the binding site of the natural ligand. Receptor effectors can modulate signal transduction when used alone, i.e. can be surrogate ligands, or can alter signal transduction in the presence of the natural ligand, either to enhance or inhibit signaling by the natural ligand. The term "antagonists" as used herein refers to molecules that block or decrease the signal transduction activity of a receptor; e.g., they can competitively, non competitively, and/or allosterically inhibit signal transduction from the receptor.

The term "agonist" as used herein refers to agents which: induce activation of receptor signaling pathways, e.g., such as by mimicking a ligand for the receptor; potentiate the sensitivity of the receptor to a ligand, e.g., lower the concentrations of ligand required to induce a particular level of receptor-dependent signaling; or otherwise enhance the signal transduction activity of a receptor.

The terms "receptor activator" and "surrogate ligand" as used herein refer to an agonist which induces signal transduction from a receptor.

"Orphan receptor" is a designation given to a receptor for which no specific natural ligand has been described and/or for which no function has been determined.

The term "endogenous gene" is intended to refer to a gene in a cell that is naturally part of the genome of the cell and which, most preferably, is present in its natural location in the genome (as opposed to "heterologous" DNA which has been introduced into the cell). Likewise, the term "endogenous protein" is intended to include proteins of a cell that are encoded by endogenous genes of the cell.

The term "heterologous promoter" as used herein, refers to a promoter that does not naturally regulate the gene to which the heterologous promoter is operatively linked. For example, an endogenous yeast gene that is not normally responsive to a signal transduction pathway of the yeast cell (e.g., a yeast pheromone response pathway) can be operatively linked to a heterologous promoter, also not normally responsive to signals produced by the transduction pathway. A fusion protein of the invention, which is engineered to be responsive to the signal transduction pathway, is used to confer signal transduction responsiveness to the endogenous yeast gene through association of the binding site of the heterologous promoter with a region of the fusion protein.

The term "indicator gene" as used herein refers to an expressible (e.g., able to be transcribed and (optionally) translated) DNA sequence which is expressed in response to activation of the fusion protein of the invention. Exemplary indicator genes include unmodified endogenous genes operatively linked to heterologous promoters.

The terms "reporter gene" and "reporter gene construct" are used interchangeably herein to refer to an indicator gene operatively linked to at least one transcriptional regulatory sequence. Transcription of the reporter gene is controlled by the transcriptional regulatory sequence to which it is operatively linked. Exemplary transcriptional control sequences are promoter sequences. Examples of promoters include, but are not limited to, Gal1, Gal10, Mel and the LexA operator. The activity of at least one or more of these control sequences is dependent on the activity of a fusion protein of the current invention, in contrast to the natural pheromone regulation of the reporter genes known in the art, (e.g., Fus1-lacZ, Fus1-HIS3, etc.; see, e.g., U.S. Pat. Nos. 5,401, 629 and 5,691,188). A reporter gene is also meant to include a promoter-reporter gene construct which is heterologously expressed in a cell.

The terms "transcriptional control element" and "transcriptional regulatory element" are used interchangeably herein, and are intended to encompass any moiety which controls/regulates transcription of a gene to which it is operatively linked, including, but not limited to, promoters, operators and enhancers which are responsive to signal transduction pathways.

As used herein, "heterologous DNA" or "heterologous nucleic acid" includes DNA that does not occur naturally as part of the genome in which it is present, or which is found in a location or locations in the genome that differs from that in which it occurs in nature. Heterologous DNA is DNA that is not naturally occurring in that position or is not endogenous to the cell into which it is introduced, but has been obtained from another cell. Generally, although not necessarily, such DNA encodes proteins that are not normally produced by the cell in which it is expressed. Heterologous DNA can be from the same species, although in preferred embodiments, it is from a different species. In particularly preferred embodiments, it is mammalian, e.g., human. Heterologous DNA may also be referred to as foreign DNA. Any DNA that one of skill in the art would recognize or consider as heterologous or foreign to the cell in which it is expressed is herein encompassed by the term heterologous DNA. Examples of heterologous DNA include, but are not limited to, DNA that encodes test polypeptides, receptors, reporter genes, transcriptional and translational regulatory sequences, or selectable or traceable marker proteins, such as a protein that confers drug resistance.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

To determine the percent homology of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). For example, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4, and a length weight of 1, 2, 3, 4, 5, or 6. In another embodiment, the percent identity between two nucleotide sequences is determined using the GAP program in the GCG software package (available at http://www.gcg-.com), using a NWSgapdna.CMP matrix and a gap weight of 40, 50, 60, 70, or 80, and a length weight of 1, 2, 3, 4, 5, or 6. In another embodiment, the percent identity between two amino acid or nucleotide sequences is determined using the algorithm of E. Meyers and W. Miller (*CABIOS,* 4:11–17 (1989)) which has been incorporated into the ALIGN program (version 2.0), using a PAM120 weight residue table, a gap length penalty of 12, and a gap penalty of 4.

The nucleic acid and protein sequences of the present invention can further be used as a "query sequence" to perform a search against public databases to identify, for example, other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al.,. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes. A "heterologous receptor" is a specific embodiment of a "heterologous protein", wherein the heterologous receptor is encoded by heterologous DNA and, upon expression of this heterologous DNA in a recombinant cell, the heterologous receptor is expressed in the recombinant cell.

The term "pheromone system protein surrogate" (abbreviated as "PSP surrogate") is intended to refer to a heterologous protein in a yeast cell which is functionally homologous to a yeast protein of the pheromone response pathway (i.e., the PSP surrogate is functionally integrated into the yeast pheromone system pathway). Examples of PSP surrogates, and methods of preparing yeast cells comprising such PSP surrogates, are described in detail in PCT Publication WO 94/23025. Preferred PSP surrogates include G protein-coupled receptors, G proteins, proteases, kinases, farnesyl transferases, carboxymethyl transferases, ABC transporters and cyclins.

The term "autocrine cell", as used herein, refers to a cell which produces a substance which can stimulate a receptor located on or within the same cell as that which produces the substance. For example, wild-type yeast MATa and MATα cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) and also express the receptor are called "autocrine cells". In some instances, such cells can also be referred to as "putative autocrine cells" since some of the cells will express peptides from the library which will not activate the receptor which is expressed. In a library of such cells, in which a multitude of different peptides are produced, it is likely that one or more of the cells will be "autocrine" in the stricter sense of the term.

II. Overview of Assay

In accordance with the assay of the invention, a cell is stimulated through contact with a test compound that interacts with a particular receptor that is either endogenous to the cell or expressed in the cell by genetic manipulations well known in the art. Upon stimulation, this receptor transmits a signal, either indirectly through a signal transduction pathway to which it is functionally coupled (as in the case of a cell surface receptor), or directly through the promotion or repression of gene expression (as in the case of an intracellular receptor). The outcome in either case is the production by the cell of a signal compound (e.g., a secreted protein). Detection of this signal compound permits an assessment of the ability of the test compound to stimulate the receptor.

In a preferred embodiment, the present invention provides a novel and sensitive Aga2 protein readout assay to assess the signal transduction activity through the pheromone response pathway in yeast. In accordance with this embodiment, a MATa yeast cell, containing a heterologous G protein-coupled receptor (GPCR), is contacted with a putative ligand ("the test compound") of the GPCR. If reactive with the ligand, the receptor stimulates increased Aga2 protein expression and cell surface presentation by the cell. The amount of Aga2 protein cell surface expression is indicative of the activity of the pheromone signaling pathway in the cell, thus indicating the ability of the test compound to activate the receptor expressed in the cell. Detection of the Aga2 protein is by specific interaction of the protein with a detector molecule conjugated with a reporter moiety. The readout from this reporter moiety indicates the presence or absence of the Aga2 protein, and thus, the activity of the pheromone response pathway in response to stimulation of the endogenous or heterologous receptor-coupled GPCR by the test compound.

In one preferred embodiment, the detection step takes place at the surface of the cell, such that the Aga2 protein remains tethered to the Aga1 protein. In a particularly preferred embodiment, the detector molecule is the Sag1p$^{21-352}$ protein.

In another preferred embodiment, the detection step of the assay takes place in a cell-free environment, such that the Aga2 protein is released from the surface of the yeast cell, either by reduction of the disulfide bonds between the Aga1 and Aga2 proteins, or by the absence of the Aga1 protein, such as in a yeast strain deleted for the AGA1 gene. In this embodiment of the subject assay, the secreted Aga2 protein is tethered to a support (e.g., a polystyrene plate or a bead) and is contacted with the detector molecule. In a particularly preferred embodiment, this detector molecule is the Sag1p$^{21-352}$ fusion protein.

In another aspect, the invention provides a kit for screening of test compounds that modulate a heterologous receptor in a cell. The kit includes a cell which comprises a heterologous receptor that is functionally integrated into a signal transduction pathway of the cell, wherein a signal molecule is produced by the cell upon activation of the signal transduction pathway; also included is a detection molecule, optionally conjugated with a reporter moiety. The kit also includes materials such as growth media, buffers appropriate for the introduction of test compounds, and reagents for quantitating the amount of detectable signal generated, and instructional materials for carrying out the screening assay. In a preferred embodiment, the invention provides a kit for the screening of potential agonist or antagonist compounds for a desired GPCR, including a MATa yeast cell, optionally containing an aga1 deletion, to be transformed with a GPCR of choice. The kit also includes a detection molecule specific for the Aga2 protein, optionally conjugated with a reporter moiety. In a particularly preferred embodiment, this detection molecule is the Sag1p$^{21-352}$ fusion protein. In another particularly preferred embodiment, this detection molecule is an anti-Aga2 antibody.

The present invention provides for the use of any type of cell in the subject assays, whether prokaryotic or eukaryotic. In preferred embodiments, the cells of the present invention are eukaryotic. In certain preferred embodiments the cells are mammalian cells. In other preferred embodiments the cells are yeast cells, with cells from the genera *Saccharomyces* or *Schizosaccharomyces* being more preferred. The host cells can be derived from primary cells, or from transformed and/or immortalized cell lines.

The subject assays provide a means for detecting the ability of compounds to modulate the signal transduction activity of the target receptor by scoring for up- or down-regulation of a detection signal. Signal transduction can be measured in a variety of ways, including but not limited to, physical and biological methods, enzymatic methods, and transcriptional activation of endogenous genes or reporter genes. For example, endogenous yeast second messenger generation (e.g., GTP hydrolysis, calcium mobilization, or phospholipid hydrolysis) or increased transcription of an endogenous gene can be detected directly. Alternatively, the use of a reporter or indicator gene can provide a convenient readout. By whatever means measured, a change (e.g., a statistically significant change) in the detection signal can be used to facilitate isolation of compounds which modulate receptor or ion channel activities.

In one embodiment of the present invention, the cells express the receptor of interest endogenously. In other embodiments, the cells are engineered to express a heterologous receptor protein. In either of these embodiments, it may be desirable to inactivate one or more endogenous genes of the cells. For example, certain preferred embodiments in which a heterologous receptor is provided utilize cells in which the gene for the homologous receptor has been inactivated. Likewise, other proteins involved in transducing signals from the target receptor can be inactivated, or complemented with an ortholog or paralog from another organism, e.g., yeast G protein subunits can be complemented by mammalian G protein subunits in yeast cells also engineered to express a mammalian G protein-coupled receptor. Other complementations include, for example, expression of heterologous MAP kinases or erk kinases, MEKs or MKKs (MAP kinase kinases), MEKKs (MEK kinases), PAKs (p21-activated kinases, e.g., Ste 20), ras and the like.

In one embodiment, the assay of the present invention can be used to screen compounds, e.g., small molecules, which are exogenously added to cells in order to identify potential receptor effector compounds. In another embodiment the subject assays enable rapid screening of large numbers of polypeptides in a library expressed in the cell in order to identify those polypeptides which agonize or antagonize receptor bioactivity, creating an autocrine system. The autocrine assay is characterized by the use of a library of recombinant cells, each cell of which includes a target receptor protein whose signal transduction activity can be modulated by interaction with an extracellular signal, the transduction activity being able to generate a detectable signal, and an expressible recombinant gene encoding an exogenous test polypeptide from a polypeptide library. By the use of a gene library, the mixture of cells collectively expresses a population of test polypeptides. In preferred embodiments, the polypeptide library includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

In another embodiment of the assay, if a test compound does not appear to directly induce the activity of the target receptor protein, the assay may be repeated and modified by the introduction of a step in which the cell is first contacted with a known activator of the target receptor to induce the signal transduction pathways from the receptor. Thus, a test compound can be assayed for its ability to antagonize, e.g., inhibit or block the activity of the activator. Alternatively, the assay can score for test compounds which potentiate the induction response generated by treatment of the cell with a known activator.

As set out above, the invention relates to methods for identifying compounds from among a set or collection or library of one or more compounds that modulate the activity of a signal transduction pathway in a cell. The pathway may be an endogenous signal transduction pathway within the cell (for example, the pheromone response pathway in a yeast cell), or may comprise one or more surrogate components which function in place of a natural component of the pathway.

Test compounds which act as agonists are detected as compounds which cause an increase in detectable signal as compared with the signal in the absence of the test compound. In another aspect, the effect of the test compounds on cells that are essentially identical except for the presence or absence of a target protein (e.g., a receptor, an ion channel, or a signal transduction pathway component surrogate) can be detected. Compounds which act as antagonists are detected as those which cause a decrease in the detectable signal generated by an agonist or a natural stimulator of signal transduction pathway when compared with the same cell in the absence of the test compound.

Alternatively, the target specificity of the test compound may be assessed by comparing the detectable signal generated in cells which differ only in the surrogate component of the signal transduction pathway. For example, cells which comprise different functionally coupled G protein-coupled receptors (GPCRs) may be compared in this way. Differences in detectable signal production may then be ascribed to the GPCRs and may be distinguished from effects due to components present in each cell. In another embodiment, the cells may differ in that one cell comprises a functional surrogate signal transduction component (e.g., mammalian GPCR) whereas the other is identical except that the natural component is substituted for the functional surrogate.

By this method, compounds which induce a signal pathway from a particular receptor or channel can be identified. If a test compound does not appear to induce the activity of the receptor/channel protein, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

The method of the present invention is useful for identifying compounds that interact with any receptor protein whose activity ultimately induces a signal transduction cascade in the cell which can be exploited to produce a detectable signal. In particular, the assays can be used to test functional ligand-receptor or ligand-ion channel interactions for cell surface-localized receptors and channels, and also for cytoplasmic and nuclear receptors. As described in more detail below, the subject assay can be used to identify effectors of, for example, G protein-coupled receptors, receptor tyrosine kinases, cytokine receptors, and ion channels, as well as steroid hormone, or other nuclear receptors. In certain embodiments the method described herein is used for identifying ligands for "orphan receptors" for which no ligand is known.

In embodiments utilizing an "autocrine cell" of the present invention, and in which cell surface receptors are the assay targets, it will be desirable for each of the peptides of the peptide library to include a signal sequence for secretion. In certain embodiments the expression of such a signal sequence may ensure appropriate transport of the peptide to the endoplasmic reticulum, the golgi, and ultimately to the cell surface. When a yeast cell is the subject cell, in certain embodiments, the signal sequence will transport peptides to the periplasmic space, however, such transport may not be necessary to achieve autocrine stimulation.

Any transfectable cell that can express the desired cell surface protein in a manner such the protein functions to transduce intracellularly an extracellular signal may be used as the cell of the invention. Similarly, any cell surface protein that is known to those of skill in the art or that may be identified by those of skill in the art may used in the assay. The cell surface protein may be endogenously expressed on the selected cell or it may be expressed from cloned DNA.

In an embodiment of the invention, the detectable signal will be generated by an endogenous gene at its natural location in the genome of the cell. The endogenous gene is naturally responsive to the signal transduction pathway of interest in the detector cell, thereby providing "endogenous signaling".

[In another embodiment of the invention, an indicator gene or "reporter gene" is inserted into the detector cell that will produce a detection signal upon activation of a signal transduction pathway of the detector cell. Typically, the indicator gene is in operative linkage with one or more transcriptional control elements, the activity of which is indirectly regulated by the signal transduction activity of the target receptor, with the level of expression of the indicator gene providing the receptor-dependent detection signal. The amount of transcription from the indicator gene may be measured using any method known to those of skill in the art to be suitable.] I suspect strongly that this paragraph runs afoul of the prior art and other SIBIA patents. I would excise it. Same with the following paragraphs.

In certain embodiments, indicator genes produce a spectrometrically active label, e.g., changes in color, fluorescence or luminescence, or a gene product which alters a cellular phenotype, e.g., cell growth, drug resistance or auxotrophy. In still other embodiments, the indicator gene encodes a gene product which confers a growth signal. In yet other embodiments, the indicator gene encodes a gene product that permits prototrophic growth, or that confers sensitivity to drugs for counterselection purposes, e.g., canavanine or cycloheximide. Examples of indicator genes, including heterologous genes as well as endogenous yeast genes that are not normally responsive to the signal transduction pathway, suitable for use in accordance with the invention include ADE1, ADE2, ADE3, ADE4, ADE5, ADE7, ADE8, ASP3, ARG1, ARG3, ARG4, ARG5, ARG6, ARG8, ARO2, ARO7, BAR1, CAT, CHO1, CYS3, GAL1, GAL7, GAL10, GFP, HIS1, HIS3, HIS4, HIS5, HOM3, HOM6, ILV1, ILV2, ILV5, INO1, INO2, INO4, lacZ, LEU1, LEU2, LEU4, luciferase, LYS2, MAL, MEL MET2, MET3, MET4, MET8, MET9, MET14, MET16, MET19, OLE1, PHO5, PRO1, PRO3, THR1, THR4, TRP1, TRP2, TRP3, TRP4, TRP5, URA1, URA2, URA3, URA4, URA5 and URA10. Preferred indicator genes include CAT, GAL1, GAL7, GAL10, GFP, HIS3, lacZ, luciferase, LEU2, MEL, PHO5, and URA3.

Transcriptional control elements for operative linking to an indicator gene, or for modifying the genomic locus of an indicator gene include, include but are not limited to, promoters, enhancers, and operators, the activities of which are responsive to cellular signal transduction pathways. An example of such a transcriptional control element is the FUS1 promoter which is activated by signal transduction through the pheromone response pathway (U.S. Pat. No. 5,063,154 to Fink et al.).

III. Host Cells

Suitable cells for generating the subject assay include prokaryotes, yeast, or higher eukaryotic cells, including plant and animal cells, especially mammalian cells. Prokaryotes include gram negative or gram positive organisms. Examples of suitable mammalian host cell lines include the COS-7 line of monkey kidney cells (ATCC CRL 1651) (Gluzman (1981) *Cell* 23:175) CV-1 cells (ATCC CCL 70), L cells, C127, 3T3, Chinese hamster ovary (CHO), HeLa, HEK-293, SWISS 3T3, and BHK cell lines.

If yeast cells are used, the yeast may be of any species which are cultivable and in which an exogenous receptor can be made to engage the appropriate signal transduction machinery of the host cell. Suitable species include *Kluyveromyces lactis, Schizosaccharomyces pombe,* and *Ustilago maydis; Saccharomyces cerevisiae* is preferred. In a preferred embodiment of the assay, the yeast cell is of the MATa mating type.

Other yeast which can be used in practicing the present invention are *Neurospora crassa, Aspergillus niger, Aspergillus nidulans, Pichia pastoris, Candida tropicalis,* and *Hansenula polymorpha*. The term "yeast", as used herein, includes not only yeast in a strictly taxonomic sense, i.e., unicellular organisms, but also yeast-like multicellular fungi or filamentous fungi.

It will be understood that to achieve selection or screening, the cell must have an appropriate phenotype. For example, generating a pheromone-responsive chimeric HIS3 gene in a yeast that has a wild-type HIS3 gene would frustrate genetic selection. Thus, to achieve nutritional selection, an auxotrophic strain is preferred.

A variety of complementations for use in the subject assay can be constructed. Indeed, many yeast genetic complementations with mammalian signal transduction proteins have been described in the art. For example, Mosteller et al. (1994) *Mol. Cell Biol.* 14:1104–12 demonstrates that human Ras proteins can complement loss of ras mutations in *S. cerevisiae*. Moreover, Toda et al. (1986) *Princess Takamatsu Symp* 17: 253–60 have shown that human Ras proteins can complement the loss of Ras 1 and Ras2 proteins in yeast, and hence are functionally homologous. Both human and yeast Ras proteins can stimulate the magnesium and guanine nucleotide-dependent adenylate cyclase activity present in yeast membranes. Ballester et al. (1989) *Cell* 59: 681–6 describe a vector to express the mammalian GAP protein in the yeast *S. cerevisiae*. When expressed in yeast, GAP inhibits the function of the human Ras protein, and complements the loss of IRA1. IRA1 is a yeast gene that encodes a protein with homology to GAP and acts upstream of Ras. Mammalian GAP can therefore function in yeast and interact with Ras yeast. Wei et al. (1994) *Gene* 151: 279–84 describes that a human Ras-specific guanine nucleotide-exchange factor, Cdc25GEF, can complement the loss of Cdc25 function in *S. cerevisiae*. Martegani et al. (1992) *EMBO J.* 11: 2151–7 describe the cloning by functional complementation of a mouse cDNA encoding a homologue of Cdc25, a *Saccharomyces cerevisiae* Ras activator. Vojtek et al. (1993) *J. Cell Sci.* 105: 777–85 and Matviw et al. (1992) *Mol. Cell Biol.* 12: 5033–40 describe how a mouse CAP protein, e.g., an adenylyl cyclase associated protein associated with Ras-mediated signal transduction, can complement defects in *S. cerevisiae*. Papasavvas et al. (1992) *Biochem. Biophys. Res. Commun.* 184:1378–85 also suggest that inactivated yeast adenylyl cyclase can be complemented by a mammalian adenylyl cyclase gene. Hughes et al. (1993) *Nature* 364: 349–52 describe the complementation of byr1 in fission yeast by mammalian MAP kinase (MEK). Parissenti et al. (1993) *Mol Cell Endocrinol* 98: 9–16 describe the reconstitution of bovine protein kinase C (PKC) in yeast. The $Ca^{2+}$ and phospholipid-dependent Ser/Thr kinase PKC plays important roles in the transduction of cellular signals in mammalian cells. Marcus et al. (1995) *P.N.A.S.* 92: 6180–4 suggest the complementation of shk1 null mutations in *S. pombe* by either the structurally related *S. cerevisiae* Ste20 or mammalian p65PAK protein kinases.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of an inactivated gene of the host cell is supplied by an exogenous nucleic acid. For instance, yeast cells can be "mammalianized", and even "humanized", by complementation of receptor and signal transduction proteins with mammalian homologs. To illustrate, inactivation of a yeast Byr2/Ste11 gene can be complemented by expression of a human MEKK gene.

In certain embodiments (particularly those in which an autocrine peptide library is employed), the growth arrest consequent to activation of the pheromone response pathway is an undesirable effect since cells that bind agonists stop growing while surrounding cells that fail to bind peptides will continue to grow. The cells of interest, then, will be overgrown or their detection obscured by the background cells, confounding identification of the compound of interest. To overcome this problem the present invention teaches engineering the cell such that: 1) growth arrest does not occur as a result of exogenous signal pathway activation (e.g., by inactivation of the FAR1 gene); and/or 2) a selective growth advantage is conferred by activating the pathway.

It is desirable that the exogenous receptor be exposed on a continuing basis to the test compound. Unfortunately, this is likely to result in desensitization of the pheromone response pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) *Mol. Cell. Biol.* 13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations, e.g., STE50, SGV1, BAR1, STE2, STE3, PIK1, MSG5, SIG1 and AFT1, have the similar effect of increasing the sensitivity of the bioassay. Thus desensitization may be avoided by mutating (which may include deleting) the SST2 gene so that it no longer produces a functional protein, or by mutating one of the other genes listed above.

IV. Expression Systems

Ligating a polynucleotide coding sequence into a gene construct, such as an expression vector, and transforming or transfecting into hosts, either eukaryotic (yeast, avian, insect or mammalian) or prokaryotic (bacterial cells), are standard procedures used in producing other well-known proteins, including sequences encoding exogenous receptor and peptide libraries. Similar procedures, or modifications thereof, can be employed to prepare recombinant reagent cells of the present invention by tissue-culture technology in accord with the subject invention.

In general, it will be desirable that the vector be capable of replication in the host cell. It may be DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (Cloning Vectors: A Laboratory Manual, Elsevier, New York, 1985). Mammalian expression vectors may comprise non-transcribed elements such as an origin of replication, a suitable promoter and enhancer linked to the gene to be expressed, other 5' or 3' flanking nontranscribed sequences, 5' or 3' nontranslated sequences, such as necessary ribosome binding sites, a poly-adenylation site, splice donor and acceptor sites, and transcriptional termination sequences.

Preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

Transcriptional and translational control sequences in expression vectors to be used in transforming mammalian cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al. (1978) *Nature* 273: 111). Smaller or larger SV40 fragments may also be used, provided the approximately 250 bp sequence extending from the Hind III site toward the Bgl I site located in the viral origin of replication is included. Exemplary vectors can be constructed as disclosed by Okayama and Berg (1983, *Mol. Cell Biol.* 3:280). A useful system for stable high level expression of mammalian receptor cDNAs in C127 murine mammary epithelial cells can be constructed substantially as described by Cosman et al. (1986, *Mol. Immunol.* 23:935). Other expression vectors for use in mammalian host cells are derived from retroviruses.

In other embodiments, the use of viral transfection can provide stably integrated copies of the expression construct. In particular, the use of retroviral, adenoviral or adeno-associated viral vectors is contemplated as a means for providing a stably transfected cell line which expresses an exogenous receptor, and/or a polypeptide library.

A number of vectors exist for the expression of recombinant proteins in yeast. For instance, YEP24, YIP5, YEPS1, YEP52, pYES2, and YRP17 are cloning and expression vehicles useful in the introduction of genetic constructs into *S. cerevisiae* (see, for example, Broach et al. (1983) in *Experimental Manipulation of Gene Expression, ed. M Inouye Academic Press*, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. Moreover, if yeast are used as a host cell, it will be understood that the expression of a gene in a yeast cell requires a promoter which is functional in yeast. Suitable promoters include the promoters for metallothionein, 3-phosphoglycerate kinase (Hitzeman et al., *J. Biol. Chem.* 255,2073 1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., *EPO Publn.* No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose, galactose and melibiose utilization. Finally, promoters that are active in only one of the two haploid mating types may be appropriate in certain circumstances. Among these haploid-specific promoters, the pheromone promoters MFa1 and MFα1 are of particular interest.

In some instances, it may be desirable to use insect cells as the host cells. In such embodiments, recombinant polypeptides can be expressed by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In constructing suitable expression plasmids, the termination sequences associated with these genes, or with other genes which are efficiently expressed in yeast, may also be ligated into the expression vector 3' of the heterologous coding sequences to provide polyadenylation and termination of the mRNA.

V. Receptors

Receptor proteins (e.g., pheromone system protein surrogates) for use in the present invention can be any receptor or ion channel which interacts with an extracellular molecule (i.e., hormone, growth factor, peptide, ion) to modulate a signal in the cell. To illustrate, the receptor can be a cell surface receptor or, in other embodiments, an intracellular receptor. In certain embodiments, the receptor is a cell surface receptor, such as: a receptor tyrosine kinase, e.g., an EPH receptor; an ion channel; a cytokine receptor; a chemokine receptor; a growth factor receptor; or a G protein-coupled receptor, such as a chemoattractant peptide receptor, a neuropeptide receptor, a light receptor, a neurotransmitter receptor, or a polypeptide hormone receptor. In a preferred embodiment, the pheromone system protein surrogate to be assayed is selected from the group consisting of G protein-coupled receptors, G proteins, proteases, kinases, farnesyl transferases, carboxymethyl transferases, ABC transporters and cyclins. In addition, the subject assay can be used to identify ligands for an orphan receptor, i.e., a receptor with no known ligand, regardless of the class of receptors to which it belongs.

In those embodiments wherein the target receptor is a cell surface receptor and the cell expresses a peptide library, it may be desirable, in certain embodiments, for the peptides in the library to express a signal sequence to ensure that the peptides are processed in the appropriate secretory pathway and thus are available to interact with receptors on the cell surface.

G Protein-Coupled Receptors.

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha (α), beta (β) and gamma (γ) subunits, are complexed with the nucleotide guanosine diphosphate (GDP) and are in contact with receptors. When a hormone or other first messenger binds to a receptor, the receptor changes conformation and this alters its interaction with the G protein. This spurs the α subunit to release GDP, and the more abundant nucleotide guanosine triphosphate (GTP), replaces it, activating the G protein. The G protein then dissociates to separate the α subunit from the still complexed beta and gamma subunits. Either the Gα subunit, or the Gβγ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the Ga converts the GTP to GDP, thereby inactivating itself. The inactivated Gα may then reassociate with the Gβγ complex.

Hundreds, if not thousands, of receptors convey messages through heterotrimeric G proteins, of which at least 17 distinct forms have been isolated. Although the greatest variability has been seen in the α subunit, several different β and γ structures have been reported. There are, additionally, many different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) *Cell* 72, 415; Kouba et al. *FEBS Lett.* (1993) 321, 173; and Birkenbach et al. (1993) *J. Virol.* 67, 2209.

The "exogenous receptors" of the present invention may be any G protein-coupled receptor, preferably exogenous to the cell, which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein-coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, histamine, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fin1p and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (lh/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, α-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate. Preferred G protein-coupled receptors include, but are not limited to: α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), rh2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2a adenosine receptor, A2b adenosine receptor, A3 adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor (FPR), fMLP-like receptor (FPRL-1), angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, CXCR1 (IL-8 receptor A), CXCR2 (IL-8 receptor B), Delta Opioid receptor, Kappa Opioid receptor, mip-1 alpha/RANTES receptor (CRR1), Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor. In addition, there are at least five receptors (CC and CXC receptors) involved in HIV viral attachment to cells. The two major co-receptors for HIV are CXCR4, (fusin receptor, LESTR, SDF1 receptor) and CCR5 (m-trophic). More preferred receptors include the following human receptors: melatonin receptor 1a, galanin receptor 1, neurotensin receptor, adenosine receptor 2a, somatostatin receptor 2 and corticotropin releasing factor receptor 1. Melatonin receptor 1a is particularly preferred. Other G protein-coupled receptors (GPCRs) are known in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include STE2, STE3, Gal1, and Gal10. Suitable signal sequences include those of STE2, STE3 and of other genes which encode proteins secreted by yeast cells. Preferably, when a yeast cell is used, the codons of the gene would be optimized for expression in yeast. See Hoekema et al., (1987) *Mol. Cell. Biol.*, 7:2914–24; Sharp, et al., (1986)14:5125–43.

The homology of STRs is discussed in Dohlman et al., *Ann. Rev. Biochem.*, (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

In certain embodiments, the endogenous yeast G protein will be sufficiently homologous to the cognate G protein which is natively associated with the wild-type exogenous G protein-coupled receptor for coupling to occur such that the receptor will be functional. For example, the human somatostatin receptor will functionally couple to the endogenous yeast GPA-1 subunit.

In other embodiments, the wild-type exogenous G protein-coupled receptor cannot be made functional in yeast, but may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible. For example, the V–VI loop of a heterologous G protein-coupled receptor could be replaced with that of the yeast STE2 or STE3 receptor).

In yet another embodiment, a compatible G protein can be provided. A compatible G protein for use in the instant assays can include a heterologous or chimeric G protein subunit (or subunits) such as those described in the art (see e.g., PCT PCT/US94/03143). Preferably, the yeast genome is modified so that it is unable to produce the yeast receptors which are homologous to the exogenous receptors in functional form.

VII. Test Compounds

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

If a test compound fails to stimulate the activity of a receptor, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

A. Exogenously Added Compounds

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. *J. Am. Chem. Soc.* 114:10987; DeWitt et al. 1993. *Proc. Natl. Acad. Sci. USA:*6909), peptoids (Zuckermann. 1994. *J. Med. Chem.* 37:2678) oligocarbamates (Cho et al. 1993. *Science* 261: 1303), and hydantoins (DeWitt et al. supra). Rebek et al. have described an approach for the synthesis of molecular libraries of small organic molecules with a diversity of 104–105 (Carell et al. 1994. *Angew. Chem. Int. Ed. Engl.* 33:2059; Carell et al. *Angew. Chem. Int. Ed. Engl.* 1994.33: 2061).

The compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. *Anticancer Drug Des.* 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. *Proc. Natl. Acad. Sci. USA* 91:11422; Horwell et al. 1996 *Immunopharmacology* 33:68; and in Gallop et al. 1994. *J. Med. Chem.* 37:1233. In addition, libraries such as those described in the commonly owned applications U.S. Ser. No. 08/864,241, U.S. Ser. No. 08/864,240 and U.S. Ser. No. 08/835,623 can be used to provide compounds for testing in the present invention.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; and Ladner, supra).

Other types of peptide libraries may also be expressed, see, e.g., U.S. Pat. Nos. 5,270,181 and 5,292,646; and PCT publication WO94/02502). In still another embodiment, the combinatorial polypeptides are produced from a cDNA library.

B. Peptide Libraries

In certain embodiments, yeast cells can be engineered to produce the compounds to be tested. This assay system has the advantage of increasing the effective concentration of the compound to be tested. In one embodiment, a method such as that described in WO 94/23025 can be utilized.

Other methods can also be used. As mentioned above, peptide libraries are systems which simultaneously display, in a form which permits interaction with a target, a highly diverse and numerous collection of peptides. Many of the systems known in the art for presentation of peptides in a library are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. Although a cell surface receptor may be used as a target, the screening will not reveal whether the binding of the peptide caused an allosteric change in the conformation of the receptor.

The Ladner et al. patent, U.S. Pat. No. 5,096,815, describes a method of identifying novel proteins or polypeptides with a desired DNA binding activity. Semi-random ("variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol. Chem.* (1989) 264, 20206 and Kaiser et al. (1987) *Science* 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/02502). The combinatorial peptide can be attached to one of the termini of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is derived to express a combinatorial library of polypeptides which are based at least in part on a known polypeptide sequence or a portion thereof (not a cDNA library). That is, the sequences of the library are semi-random, being derived by combinatorial mutagenesis of a known sequence. (See, e.g., Ladner et al. PCT publication WO 90/02909; Garrard et al., PCT publication WO 92/09690; Marks et al. (1992) *J. Biol. Chem.* 267:16007–16010; Griffiths et al. (1993) *E.M.B.O. J* 12:725–734; Clackson et al. (1991) *Nature* 352:624–628; and Barbas et al. (1992) *P.N.A.S.* 89:4457–4461). Accordingly, polypeptides which are known ligands for a target receptor can be mutagenized by standard techniques to derive a variegated library of polypeptide sequences which can further be screened for agonists and/or antagonists. This library can be expressed in a reagent cell of the present invention, and other receptor activators can be isolated from the library. This has permitted the identification of even more potent FPRL-1 surrogate ligands (Klein et al., supra).

Alternatively, the library can be expressed under conditions wherein the cells are in contact with the original tridecapeptide, e.g., the FPRL-1 receptor is being induced by that surrogate ligand. Peptides from an expressed library can be isolated based on their ability to potentiate the induction, or to inhibit the induction, caused by the surrogate ligand. The latter, of course, will identify potential antagonists of chemoattractant receptors. In still other embodiments, the surrogate ligand can be used to screen exogenous compound libraries (peptide and non-peptide) which, by modulating the activity of the identified surrogate, will presumably also similarly effect the native ligand's effect on the target receptor. In such embodiments, the surrogate ligand can be applied to the cells, though is preferably produced by the reagent cell, thereby providing an autocrine cell.

In still another embodiment, the combinatorial polypeptides are produced from a cDNA library.

In a preferred embodiment of the present invention, the yeast cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

C Periplasmic Secretion

In those embodiments of the invention in which yeast cells are used as the host cell and the compounds tested are endogenously expressed from a library, it will be noted that the yeast cell is bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Because this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the α-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

EXEMPLIFICATION

The invention will be more readily understood by reference to the following examples, which are included merely for purposes of illustration of certain aspects and embodiments of the present invention and are not intended to limit the invention.

Example 1

Construction of Strains

The yeast plasmids and strains used in the following examples are set forth in Tables 1 and 2, respectively.

TABLE 1

Plasmids Utilized in the Experiments

| Plasmid | Genetic markers |
|---|---|
| Cp1015 | URA3 CEN6 ARSH4 AmpR |
| Cp2695 | PGKp-ML1aR LEU2 2mu-ori REP3 AmpR |
| Cp4258 | PGKp-MFα1(1–89)-PHO5t LEU2 2mu-ori REP3 AmpR |
| Cp4261 | PGKp-MFα1(1–89)-NocR-PHO5t LEU2 2mu-ori REP3 AmpR |
| Cp4271 | leu2-d 2mu-ori AmpR |
| Cp5075 | PGKp-MFα1(1–89)-NPY-Y1R-HA-PHO5t LEU2 2mu-ori REP3 AmpR |
| Cp5893 | hisG-URA3-hisG AmpR |
| Cp6444 | PGKp-MFα1(1–89)-(His)$_6$-Xpress-SAG1(21–352) leu2-d 2mu-ori AmpR |
| Cp6656 | HA-AGA2 URA3 CEN6 ARSH4 AmpR |
| Cp6658 | AGA2-HA URA3 CEN6 ARSH4 AmpR |
| Cp6661 | Ptrc-(His)$_6$-Xpress-SAG1(21–352) lacI AmpR |
| Cp6710 | aga1::hisG-URA3-hisG AmpR |

TABLE 2

S. cerevisiae Strains Utilized in the Experiments

| Strain | Genotype |
|---|---|
| CY1892 | MATa bar1::hisG tbt1-1 trp1 his3 leu2 ura3 FUS1p-HIS3 |
| CY17353 | MATa bar1::hisG ste2Δ tbt1-1 trp1 his3 leu2 ura3 FUS1p-HIS3 |
| CY17880 | MATa bar1::hisG sst2Δ ste2Δtbt1-1 trp1 his3 leu2 ura3 FUS1p-HIS3 |
| CY19890 | MATa aga1::hisG sst2Δ ste2Δ bar1::hisG tbt1-1 trp1 his3 leu2 ura3 FUS1p-HIS3 |
| CY19652 | MATα leu2-3, 112 his3-11, 15 pep4Δ |

The plasmids utilized in the experiments detailed in the Exemplification are listed in Table 1. The plasmids Cp6656 and Cp6658 encoding the Aga2p tagged with the hemagglutinin (HA) epitope at the N-terminus or at the C-terminus, respectively, have been constructed as follows. Several fragments of AGA2 gene were PCR amplified using S. cerevisiae genomic DNA as a template and the following primers: fragment 1, primers AGA2-5Xho: 5'-GCAGCTCGAGTTTTCTGTATAATTCATTCGCGAGG-3' (set forth in SEQ ID NO:1), and AGA2-RevN: 5'-AGCGTAATCTGGAACATCGTATGGGTATATAGTTGT-CAGTTCCTGTGCTAAAAC-3' (set forth in SEQ ID NO:2); fragment 2, primers AGA2-For N: 5'-TACCCATACGATGTTCCAGATTACGCTTGCGAG-CAAATCCCCTCACCAAC-3' (set forth in SEQ ID NO:3) and AGA2-3Bam: 5'-GCAGGGATCCTGGTTGTTCCG-TACCGGAACAC-3' (set forth in SEQ ID NO:4); fragment 3, primers AGA2-5Xho and AGA2-RevC: 5'-AGCG-TAATCTGGAACATCGTATGGGTAAAAAA-CATACTGTGTGTTTATGGGGCTG-3' (set forth in SEQ ID NO:5); fragment 4, primers AGA2-For C: 5'-TACGAT-GTTCCAGATTACGCTGCTTGAGCCTTC-CCCCCCAAGTTTCC-3' (set forth in SEQ ID NO:6) and AGA2-3Bam. The equimolar mixtures of fragments 1 and 2 or fragments 3 and 4 were used as templates for PCR together with the primers AGA2-5Xho and AGA2-3Bam. As a result two DNA fragments were generated that include the AGA2 gene bearing the HA epitope-encoding sequence inserted either between 24th and 25th codons or immediately downstream from the last codon of the coding sequence, respectively. Both fragments were digested with XhoI and BamHI and subcloned into the corresponding sites of a yeast low copy vector Cp1015. This gave rise to the plasmids Cp6656 and Cp6658 that encode the Aga2p bearing the HA epitope (YPYDVPDYA) in the N-terminal portion (between 7th and 8th residue of mature protein), or at the C-terminus, respectively.

A yeast vector Cp6444 for the expression of $Sag1p^{21-352}$ has been constructed as described below. A DNA fragment encoding the N-terminal portion of the Sag1p without the signal peptide (residues 21–352) was amplified by PCR using *S. cerevisiae* total chromosomal DNA as a template and the primers SAG1-5NS-Bgl: 5'-GCAGTAGATCT-TAATATCAACGATATCACATTTTCCAATTTAG-3' (set forth in SEQ ID NO:7) and SAG1-352stopXho: 5'-GCAGCTCGAGTTAATACGCACTAGTGTT-TATACTTGTTAAATCAG-3' (set forth in SEQ ID NO:8). The PCR fragment was treated with BglII and XhoI and subcloned into the plasmid pTrcHisB (Invitrogen) digested with BamHI and XhoI. The resulting plasmid was digested with NcoI and HindIII to release a fragment which encodes the $Sag1p^{21-352}$ bearing a polyhistidine tag, an Xpress epitope and an enterokinase cleavage site at the N-terminus. The latter fragment was ligated with the plasmid Cp4271 digested with BamHI and HindIII and the BglII-NcoI fragment from plasmid Cp4258 including the PGK promoter and a sequence encoding the leader sequence of prepro-α-factor.

A plasmid for a knockout of the AGA1 gene was constructed using two AGA1 fragments amplified by PCR using *S. cerevisiae* chromosomal DNA and the following pairs of primers: AGA1-Xho: 5'-GCAGCTCGAGTGCCTTG-GCATCTGATCCAGAAAC-3' (set forth in SEQ ID NO:9) and AGA1-EcoR: 5'-GCAGGAATTCGAGGTAGATGTA-GAGCTTGGAGATG-3' (set forth in SEQ ID NO:10) or AGA1-Xba: 5'-GCAGTCTAGAGTGTCATTATACAGC-CCATCCACAC-3' (set forth in SEQ ID NO:11) and AGA1-Sac: 5'-TCGCAGGAGCTCACTGGTGACTGTTCGA-CACTTAGTG-3' (set forth in SEQ ID NO:12). The fragments were digested with XhoI and EcoRI or with XbaI and SacI, respectively, and subsequently subcloned into the corresponding sites of the plasmid Cp5893 (pBL63). The resulting plasmid, which includes the AGA1 gene disrupted with the hisG-URA3-hisG fragment, was designated Cp6710.

The *S. cerevisiae* strains utilized in the experiments detailed in the Exemplification are listed in Table 2. An aga1 knockout mutation in strain CY1892 was generated as follows. Strain CY1892 was transformed with the aga1::hisG-URA3-hisG fragment from the plasmid Cp6710, digested with XhoI and SacI. The isolated Ura$^+$ transformants were propagated in YEPD medium and transferred to minimal medium supplemented with 5-fluororotic acid (FOA). Disruption of the chromosomal AGA1 gene in several FOA-resistant colonies was confirmed by colony PCR. One of the aga1 mutants isolated was designated CY19890.

Example 2

Induction of the Aga2 Protein Mediated by Heterologous G Protein-Coupled Receptors This example demonstrates the utility of the assay system of the present invention for the detection of the activity of the mating factor response pathway in response to activation of a pathway-coupled receptor by its cognate ligand. Similarly, this system can be used to determine the agonist or antagonist activity of a test compound for a given receptor coupled to the aforementioned pathway, and also to identify ligands for orphan receptors coupled to this pathway.

The assay system comprises a MATa *S. cerevisiae* yeast cell having a heterologous G protein-coupled receptor functionally coupled to the pheromone response pathway, one or more test compounds, and a detection mechanism. Binding of cognate ligand to the G protein-coupled receptor in the cell activates the receptor, causing a signal to be transduced through the functionally coupled pheromone response pathway, ultimately resulting in the expression and cell surface presentation of the Aga2 gene product. Expression of the AGA2 gene is specifically measured by the detection mechanism, which comprises a detector molecule which specifically binds to the Aga2 protein, conjugated with a reporter moiety. The readout from this reporter moiety enables a determination of the expression level of the Aga2 protein; the expression level is indicative of the activity of the pheromone response pathway in the cell, and thus, of the ability of the test compound to agonize or antagonize the pathway-linked G protein-coupled receptor.

Yeast cells coexpressing either the endogenous yeast receptor Ste2p, or a heterologous G protein-coupled receptor (human melatonin 1a receptor, nociceptin receptor, or neuropeptide Y receptor) and the Aga2 protein tagged with HA at the C-terminus (Aga2-HA) were incubated in the absence or the presence of increasing concentrations of an appropriate ligand (α-factor, melatonin, nociceptin, or neuropeptide Y, respectively) in SC-Leu media, pH 6.8. The cells ($TOD_{600}$=1.5) were pelleted, washed with ice-cold 0.15 M sodium chloride, resuspended in 50 microliters of 25 mM Tris-HCl, pH 8.5, supplemented with 10 mM dithiothreitol (DTI) and incubated for1 hour at 4° C. This DTT incubation step reduced the disulfide bonds between the Aga1 and Aga2 proteins, thereby releasing Aga2 into the extracellular medium. After centrifugation, 50 microliter aliquots of the supernatants were subjected to Western blot analysis. Immunoreactive bands corresponding to Aga2-HA were visualized using HA.11 antibodies (BAbCo) as primary antibodies, sheep anti-mouse IgG conjugated with horseradish peroxidase (Amarsham Pharmacia Biotech) as secondary antibodies, and peroxidase substrate (e.g., tetramethyl benzidine (Pierce)) for a visual readout. In each sample, a substantial increase in the expression level of the Aga2 protein was observed. In the absence of an appropriate ligand, the basal expression of the Aga2 protein was virtually undetectable. This indicated that both the endogenous Ste2 receptor and also the heterologous G protein-coupled receptors utilized in this experiment could mediate the induction of Aga2 expression in a ligand-dependent manner.

Western blot analysis is a qualitative, rather than quantitative methodology. To determine the induction of expression of the Aga2 protein quantitatively, an ELISA strategy was utilized. Cells were cultured, treated, and the Aga2 protein extracted from the cell surface by DTT incubation, as above. Aliquots of these DTT extracts (50 microliters in the case of cells utilizing the Ste2 receptor and 5 microliters in other cases) were diluted to 100 microliters with 100 mM sodium bicarbonate, pH 9.5. Samples were incubated in 96-well polystyrene plates at 4 degrees C overnight. Plates were washed three times with PBS, pH 7.2 supplemented with 0.1% Tween 20 and blocked with the same buffer containing 3% bovine serum albumin at 37° C. for 1 hr. After blocking, the plates were incubated subsequently with 5000- fold diluted HA.11 antibodies (BAbCo) and 5000-fold diluted sheep anti-mouse IgG conjugated with horseradish peroxidase (Amersham Pharmacia Biotech). Each incubation was conducted at room temperature for 1 hr and was followed by three washes with PBS, pH 7.2, 0.1% Tween 20. The peroxidase activities in each well were determined using tetramethyl benzidine as a substrate. The results of this assay appear in Table 3.

TABLE 3

Ligand-Dependent Induction of Cell Surface Aga2-HA Protein Mediated by Ste2p and Heterologous G Protein-Coupled Receptors

| Receptor | [Ligand], M[a] | HRP activity | Induction factor | $EC_{50}$, M |
|---|---|---|---|---|
| Ste2p | 0 | 0.167 | 15 | $5.9 \times 10^{-8}$ |
|  | $7.81 \times 10^{-9}$ | 0.280 |  |  |
|  | $3.13 \times 10^{-8}$ | 0.548 |  |  |
|  | $1.13 \times 10^{-7}$ | 2.163 |  |  |
|  | $5 \times 10^{-7}$ | 2.498 |  |  |
|  | $2 \times 10^{-6}$ | 2.332 |  |  |
| ML1aR | 0 | 0.065 | 19 | $2.9 \times 10^{-8}$ |
|  | $4.88 \times 10^{-10}$ | 0.154 |  |  |
|  | $1.95 \times 10^{-9}$ | 0.278 |  |  |
|  | $7.81 \times 10^{-9}$ | 0.427 |  |  |
|  | $3.13 \times 10^{-8}$ | 0.767 |  |  |
|  | $1.13 \times 10^{-7}$ | 0.829 |  |  |
|  | $5 \times 10^{-7}$ | 1.216 |  |  |
|  | $1 \times 10^{-6}$ | 1.112 |  |  |
| NocR | 0 | 0.097 | 4.2 | $1.2 \times 10^{-6}$ |
|  | $1.13 \times 10^{-7}$ | 0.097 |  |  |
|  | $2.5 \times 10^{-7}$ | 0.145 |  |  |
|  | $5 \times 10^{-7}$ | 0.240 |  |  |
|  | $1 \times 10^{-6}$ | 0.162 |  |  |
|  | $2 \times 10^{-6}$ | 0.409 |  |  |
|  | $4 \times 10^{-6}$ | 0.370 |  |  |
| NPY-Y1R | 0 | 0.131 | 2.9 | n.d.[b] |
|  | $2.5 \times 10^{-6}$ | 0.194 |  |  |
|  | $5 \times 10^{-6}$ | 0.375 |  |  |

[a]The ligands used were α-factor, melatonin, nociceptin and neuropeptide Y for Ste2p, ML1aR, nociceptin receptor and neuropeptide Y-Y1 receptor, respectively.
[b]n.d., not determined Both Ste2p and ML 1 aR were able to mediate an approximately 20-fold stimulation of Aga2 protein expression in response to ligand binding. NocR and NPY-Y1 promoted lesser induction levels of the Aga2 protein upon interaction with their cognate ligands; a 4-fold and 3-fold induction of cell-surface Aga2 protein, respectively, was observed with these receptors. This is reflected in the $EC_{50}$ determined for two of the GPCR ligands: the $EC_{50}$ of melatonin for Aga2 production in ML1aR-containing cells was 29 nM, while the $EC_{50}$ for nociceptin in NocR-containing cells was 1.2 µM.

The strong induction of Aga2 protein expression at the cell surface in response to activation of an endogenous or heterologous yeast pheromone pathway-linked G protein-coupled receptor, taken together with its low basal expression, showed that this protein serves as a good indicator for the ability of a test compound to agonize or antagonize a receptor functionally linked to this pathway.

Example 3

Detection of Endogenous Aga2 protein Using the N-terminal Domain of the α-Agglutinin Sag1 Protein The previous experiment demonstrated the utility of detecting expression of the Aga2 protein in assessing the ability of a test compound to agonize or antagonize a G-protein coupled receptor linked to the yeast pheromone response pathway. In lieu of utilizing antibodies specific to a hemagglutinin tag fused to the Aga2 protein, it was preferable to detect the Aga2 protein directly through interactions with its natural binding partner, the yeast α-agglutinin, encoded by the SAG1 gene. The Aga2 protein binds with high affinity to the N-terminal domain of the Sag1 protein in vitro, via an N-terminal binding domain. It has been demonstrated that the isolated N-terminal domain (Sag1p$^{21-352}$) retains full binding activity for a-agglutinin, and therefore represents the Aga2 protein-binding domain (Wojciechowicz et al. (1993) *Mol Cell. Biol.* 13:2554–2563).

An expression system for Sag1p$^{21-352}$ was developed in order to investigate the utility of this polypeptide for development of the Aga2 assay. A yeast high copy vector for expression of an α-factor leader-Sag1p$^{21-352}$ fusion protein under control of the PGK promoter has been constructed as described. The leader sequence of the fusion protein is separated from the Sag1 coding region by an intervening region including coding sequences for a (His)$_6$ tag, an Xpress epitope and an enterokinase cleavage site. The cultures of strain CY19652 transformed with Sag1p$^{21-352}$ expression vector Cp6444 or with control plasmid Cp4271 were grown in the medium containing 2% glucose and 2% peptic peptone (Amersham Pharmacia Biotech) for 24 hr. SDS-PAGE analysis of the culture media of strains expressing the Sag1p$^{21-352}$ demonstrated the presence of a major protein band having a molecular mass of 55 kDa which was absent in the media of the control strain. This band was recognized by anti-Xpress antibodies, indicating that it corresponded to the Sag1p$^{21-352}$. The Sag1p$^{21-352}$ was highly N-glycosylated, since the corresponding band could be visualized by staining with Amido Black or by Western blot only after treatment with Endoglycosidase. H. The levels of the Sag1p$^{21-352}$ in the media as estimated by SDS-PAGE were approximately 20 mg/L.

The Sag1p$^{21-352}$ was purified by affinity chromatography using a nickel-charged resin, ProBond (Invitrogen), according to a manufacturer's protocol. The purity of the protein was analyzed by SDS-PAGE followed by transfer to PVDF membrane and staining with AmidoBlack, and was estimated to be >95% pure, with a molecular mass of approximately 55 kDa.

To ensure that this truncation of the Sag1 protein retained full binding activity to α-agglutinin, and more specifically, the Aga2 protein, binding assays were performed. The cultures of strain CY1892 were incubated either in the absence or in the presence of 100 nM α-factor in SC media, pH 5.5. The cells (TOD$_{600}$=1) were pelleted and resuspended in 0.15 ml of the same media supplemented with varying concentrations of Sag1p$^{21-352}$. After incubation at 30° C. for 30 min, the cells were washed three times with the same media and incubated in the presence of 2% SDS for 5 min to release Sag1p$^{21-352}$ bound to the cell surface. The SDS extracts were subjected to Western blot analysis. The immunoreactive bands corresponding to Sag1p$^{21-352}$ were visualized using anti-Xpress antibodies (Invitrogen), as above. It was found that Sag1p$^{21-352}$ bound to the cell surface of intact MATa cells only after these cells were treated with α-factor and thus had been stimulated to express α-agglutinin at the cell surface.

This evidence was further corroborated by a series of ELISA-like assays. In these assays, cells of yeast strains CY1892 and CY17353 transformed with the plasmid Cp2695 were incubated either in the presence of increasing concentrations of ligand (α-factor or melatonin, respectively) or in the absence of the ligand, as described previously. Extraction of the endogenous Aga2 protein was effected with DTT, as before. Aliquots (25 microliters) of extracts were diluted with 75 microliters of 100 mM sodium bicarbonate, pH 9.5 and the resulting samples were incubated in 96-well polystyrene plates at 4° C. overnight.

A first assay was performed with yeast strain CY1892 expressing endogenous Ste2 receptor, and using α-factor as a ligand. After washing the plates three times with PBS, pH 6.5, supplemented with 0.1% Tween 20, samples were blocked with the same buffer containing 3% bovine serum albumin at 37° C. for 1 hour. After blocking, the plates were incubated subsequently with EndoH-treated $Sag1p^{21-352}$ solution (0.5 mg/ml), 1000-fold diluted anti-Xpress antibodies (Invitrogen) and 5000-fold diluted sheep anti-mouse IgG conjugated with horseradish peroxidase (Amersham Pharmacia Biotech). Both $Sag1p^{21-352}$ and antibodies were dissolved in PBS, pH 6.5 supplemented with 3% BSA. Each incubation was conducted at room temperature for 1 hr and was followed by three washes with PBS, pH 6.5, 0.1% Tween 20. Finally, the peroxidase activities in each well were determined using tetramethyl benzidine as a substrate. If the Aga2 protein were present in the plate, the $Sag1p^{21-352}$ should bind to it, the anti-Xpress antibody binds to the $Sag1p^{21-352}$ fusion protein, and the sheep anti-mouse IgG antibodies bind specifically to the anti-Xpress antibody. The results of the peroxidase assay indicated that there was a dose-dependent response in induction of the Aga2 protein by α-factor in yeast cells containing the Ste2 receptor and by melatonin in yeast cells containing the ML1a receptor, with an $EC_{50}$ of 37 nM for the former.

A second assay was performed utilizing yeast strain CY17353, transformed with plasmid Cp2695, (encoding the ML1a receptor), and using melatonin as the ligand. After blocking with 3% bovine serum albumin as before, the plates bearing the Aga2 protein were incubated with $Sag1p^{21-352}$ that had been directly conjugated with horseradish peroxidase by means of glutaraldehyde. In this assay system, Aga2 protein induction by melatonin in ML1a receptor-containing cells was also observed, with an $EC_{50}$ of 0.21 μM.

While these results did not present direct evidence that $Sag1p^{21-352}$ binds to the Aga2 protein, the data clearly indicated that the N-terminal domain of α-agglutinin interacted with the yeast cell surface in a ligand-dependent manner and therefore could be used as a tool for the development of yeast-based functional assays for G protein-coupled receptors.

Experiment 4

Whole Cell Binding Assays

A whole cell binding assay for the determination of the agonist or antagonist properties of a test compound for an endogenous or heterologous receptor functionally coupled to the yeast pheromone response pathway can be performed. In this assay, a culture of a yeast strain expressing a G protein-coupled receptor is treated with a test compound and is subsequently incubated with a $Sag1p^{21-352}$ molecule fused to a reporter moiety (e.g., β-lactamase, peroxidase, luciferase, or alkaline phosphatase). The cells are washed and incubated in the presence of an appropriate substrate for the reporter protein. The readout from the reporter moiety indicates the level of the Aga2 protein expressed on the surface of the subject cells.

In a particular example of this assay system, the $Sag1p^{21-352}$ is labeled with a fluorophore. The binding of this labeled fusion protein to the Aga2 protein at the surface of the yeast cell is monitored using a fluorescence polarization technique, such as that used previously to study binding of various lectins to the yeast cell wall (Oda et al. (1998) Biol. Pharm. Bull. 21: 1215–1217).

Experiment 5

Scintillation Proximity Assays

The fact that the Aga2 protein can be readily dissociated from the Aga1 protein and hence, from the surface of the yeast cell, by incubation of the cell with a reducing agent, makes it possible to perform assays for the detection of the Aga2 protein in a cell-free environment.

Such an assay is performed by contacting a yeast cell expressing an endogenous or heterologous G protein-coupled receptor in functional linkage with the pheromone response pathway with a test compound. Subsequently, the cells are treated with a reducing agent such as DTT. Because DTT exhibits reduced activity at pH values lower than 7.0, alternative reducing agents may be employed which are active at lower pH values (e.g., TRIS-(2-carboxyacyl)phosphine (TCEP)). Any Aga2 protein present at the cell surface is shed into the extracellular medium. Alternatively, an AGA1 deletion strain may be utilized; this strain lacks expression of the Aga1 protein that normally tethers the Aga2 protein to the extracellular surface of the yeast cell. In the absence of the Aga1 protein, the Aga2 protein is shed into the extracellular medium. Proteins in the medium are immobilized to a support such as a polystyrene plate or a bead. The presence of the Aga2 protein is ascertained by incubation with a detector molecule specific for the Aga2 protein, such as an anti-Aga2 antibody or the $Sag1p^{21-352}$ fusion protein. A reporter moiety on the detector molecule permits a quantitative readout. The presence of the Aga2 protein is indicative of activation of the pheromone response pathway, and the ability of the test compound to stimulate the endogenous or heterologous G protein-coupled receptor functionally linked to this pathway is thereby assessed.

A particular embodiment of these types of cell-free Aga2 assays is the scintillation proximity assay. In this technique, the extracellular medium potentially containing the Aga2 protein is incubated with antibodies specific for Aga2. These antibodies are also biotinylated, and thus the antibody-Aga2 complex can be tethered to the surface of SPA beads coated with streptavidin (and also containing scintillant). $Sag1p^{21-352}$ is radiolabeled with, e.g., $^{125}I$ or $^{3}H$, and is incubated with the Aga2-loaded beads. Binding of the fusion protein to the immobilized Aga2 protein brings the radiolabel in proximity to the scintillant contained within the beads, resulting in the emission of light. This emission can be readily quantitated using a scintillation counter. The presence of light indicates the presence of the Aga2 protein, and thus that the pheromone response pathway was activated in the yeast cells by the test compound via the G protein coupled receptor.

The following experiment was conducted in order to test the utility of the scintillation proximity assay for the detection of Aga2p induction mediated by heterologous receptors in yeast. An exponential phase culture of the aga1 mutant strain CY19890 transformed with the plasmid Cp2695 encoding ML1aR and Cp6656 encoding HA-tagged Aga2p was incubated in the SC-Leu medium, pH 6.8, in the absence or in the presence of 1 µM melatonin for 4 hr. One hundred microliter aliquots of culture media were placed into a 96-well plate and the following solutions were added to each well: 20 µl of 0.5 M sodium phosphate, pH 6.0, 1.5 M sodium chloride, 1% Tween 20, 10% BSA; 0.25 µg of SPA beads (Amersham) coated with biotinylated HA.11 antibodies (BAbCo) in 25 µl of PBS (20 mM sodium phosphate, pH 7.2, 0.15 M sodium chloride) and 25 µl of PBS containing [$^{125}$I]-Sag1p$^{21-352}$ (250,000 cpm). SPA beads were prepared as follows. Fifty milligrams of streptavidin-coated yttrium silicate beads were incubated in 2 ml of PBS containing 1% BSA, 0.1% Tween 20 and 0.5 mg biotinylated HA. 11 antibodies for 4 hr at room temperature. The beads were washed three times with PBS and resuspended in 1 ml of the same buffer. Sag1p$^{21-352}$ was iodinated according to standard protocols using lactoperoxidase.

Light emission was quantitated using a scintillation counter after incubation of the plate at room temperature for 1 hr, 2 hr and 6 hr. An approximately 3-fold increase in the levels of HA-tagged Aga2p in the culture media in response to melatonin was detected using the described technique (Table 4). This indicates that the scintillation proximity-based assay represents a useful method to monitor the Aga2 p induction mediated by heterologous G protein-coupled receptors expressed in yeast.

TABLE 4

Determination of Aga2-HA Induction Mediated by ML1aR by a Scintillation Proximity Assay

| Incubation time | CPM | | Induction factor |
|---|---|---|---|
| | − melatonin | + melatonin | |
| 1 hr | 2052 | 5059 | 2.5 |
| 2 hr | 2268 | 6019 | 2.6 |
| 6 hr | 3147 | 9613 | 3.1 |

INCORPORATION BY REFERENCE

All patents, published patent applications and other references disclosed herein are hereby expressly incorporated herein in their entireties by reference.

EQUIVALENTS

Those skilled in the art will recognize, or will be able to ascertain using no more than routine experimentation, many equivalents to the specific embodiments of the invention described herein. Such equivalents are intended to be encompassed by the following claims.

What is claimed is:

1. A method for identifying a test compound that modulates a heterologous receptor in a MATα *Saccharomyces cerevisiae* cell, said method comprising: providing a MATα *Saccharomyces cerevisiae* cell which comprises a heterologous receptor that is functionally integrated into a pheromone response pathway of said cell, wherein said cell has the endogenous AGA1 gene deleted, such that the AGA2 protein is secreted upon activation of said pheromone response pathway; contacting said cell with a test compound; and detecting a change in the level of expression of said AGA2 protein, thereby identifying a test compound that modulates said heterologous receptor.

2. The method of claim 1, wherein said detection step comprises: binding of said secreted AGA2 protein to a support; incubating said support with a detector molecule conjugated with a reporter moiety; and measuring the readout from said reporter moiety.

3. The method of claim 2, wherein said support comprises streptavidin-coated SPA beads containing scintillant.

4. The method of claim 3, wherein binding of said secreted Aga2 protein to said support is mediated by a biotinylated antibody, wherein said antibody binds specifically to the secreted Aga2 protein and also to said streptavidin-coated bead.

5. The method of claim 2, wherein said detector molecule is the Sag1 protein.

6. The method of claim 2, wherein said reporter moiety comprises a polypeptide selected from the group consisting of beta-lactamase, peroxidase, luciferas, and alkaline phosphatase.

7. The method of claim 2, wherein said reporter moiety is a radiolabel.

8. The method of claim 7, wherein said radiolabel is $^{125}$I or $^{3}$H.

9. The method of claim 2, wherein said readout measuring step comprises detection of emitted light.

10. The method of claim 1, wherein said heterologous receptor is a G-protein coupled receptor.

11. The method of claim 1, wherein said heterologous receptor is selected from the group consisting of melatonin receptor 1a, galanin receptor 1, nourotensin receptor, adenosine receptor 2a, somatostatin receptor 2, and corticotropin releasing factor receptor 1.

12. The method of claim 11, wherein said heterologous receptor is melatonin receptor 1a.

13. The method of claim 10, wherein said heterologous G-protein coupled receptor functionally couples to the endogenous yeast GPA-1 protein subunit.

14. The method of claim 2, wherein said reporter moiety is a fluorophore.

15. The method of claim 2, wherein said readout measuring step comprises a fluorescence polarization technique.

* * * * *

SEQUENCE LISTING

<160> NUMBER OF SEQ ID NOS: 12

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 1
gcagctcgag ttttctgtat aattcattcg cgagg                35

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 2
agcgtaatct ggaacatcgt atgggtatat agttgtcagt tcctgtgcta aaac        54

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 3
tacccatacg atgttccaga ttacgcttgc gagcaaatcc cctcaccaac          50

<210> SEQ ID NO 4
<211> LENGTH: 32

```
<212> TYPE: DNA
<213> ORGANISM: Artificial Sequence
<220> FEATURE:
<223> OTHER INFORMATION: Description of Artificial Sequence: primer

<400> SEQUENCE: 4
gcagggatcc tggttgttcc gtaccggaac ac                          32

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 5
agcgtaatct ggaacatcgt atgggtaaaa aacatactgt gtgtttatgg ggctg    55

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 6
tacgatgttc cagattacgc tgcttgagcc ttcccccca agtttcc              47

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 7
gcagtagatc ttaatatcaa cgatatcaca ttttccaatt tag                 43

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 8
gcagctcgag ttaatacgca ctagtgttta tacttgttaa atcag               45

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 9
gcagctcgag tgccttggca tctgatccag aaac                           34

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 10
```

-continued

```
gcaggaattc gaggtagatg tagagcttgg agatg                              35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 11
gcagtctaga gtgtcattat acagcccatc cacac                              35

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 12
tcgcaggagc tcactggtga ctgttcgaca cttagtg                            37
```